(12) United States Patent
Greene, Jr. et al.

(10) Patent No.: US 10,555,738 B2
(45) Date of Patent: Feb. 11, 2020

(54) EMBOLIC CONTAINMENT

(71) Applicant: MicroVention, Inc., Aliso Viejo, CA (US)

(72) Inventors: George R. Greene, Jr., Costa Mesa, CA (US); Ivan Sepetka, Los Altos, CA (US); Cathy Lei, Chino Hills, CA (US); Alejandro Berenstein, New York, NY (US); Monika Killer-Oberpfalzer, Salzburg (AT); Heath Bowman, Trabuco Canyon, CA (US)

(73) Assignee: MicroVention, Inc., Aliso Viejo, CA (US)

(*) Notice: Subject to any disclaimer, the term of this patent is extended or adjusted under 35 U.S.C. 154(b) by 283 days.

(21) Appl. No.: 15/786,393

(22) Filed: Oct. 17, 2017

(65) Prior Publication Data

US 2018/0070955 A1 Mar. 15, 2018

Related U.S. Application Data

(63) Continuation-in-part of application No. 15/599,284, filed on May 18, 2017.

(60) Provisional application No. 62/338,395, filed on May 18, 2016, provisional application No. 62/338,387, filed on May 18, 2016, provisional application No. 62/338,405, filed on May 18, 2016.

(51) Int. Cl.
*A61B 17/12* (2006.01)

(52) U.S. Cl.
CPC .. *A61B 17/12186* (2013.01); *A61B 17/12031* (2013.01); *A61B 17/12109* (2013.01); *A61B 17/12168* (2013.01); *A61B 2017/1205* (2013.01)

(58) Field of Classification Search
CPC ........ A61B 17/12181; A61B 17/12186; A61B 17/1219; A61B 17/12195
See application file for complete search history.

(56) References Cited

U.S. PATENT DOCUMENTS

| | | | |
|---|---|---|---|
| 4,921,484 A | 5/1990 | Hillstead | |
| 5,951,599 A | 9/1999 | McCrory | |
| 6,346,117 B1 | 2/2002 | Greenhalgh | |
| 6,428,558 B1 | 8/2002 | Jones et al. | |
| 6,994,717 B2 | 2/2006 | Kónya et al. | |
| 7,354,445 B2 | 4/2008 | Nicholson et al. | |
| 7,695,488 B2 | 4/2010 | Berenstein et al. | |
| 8,142,456 B2 | 3/2012 | Rosqueta et al. | |
| 8,562,667 B2 | 10/2013 | Cox | |
| 8,690,907 B1 | 4/2014 | Janardhan et al. | |

(Continued)

FOREIGN PATENT DOCUMENTS

WO    WO 2007/140797 A1    12/2007

OTHER PUBLICATIONS

WIPO, U.S. International Search Authority, International Search Report and Written Opinion dated Aug. 24, 2017 in International Patent Application No. PCT/US2017/033375, 8 pages.

*Primary Examiner* — Todd J Scherbel
(74) *Attorney, Agent, or Firm* — Inskeep IP Group, Inc.

(57) ABSTRACT

Devices, systems, and methods used to seal a treatment area to prevent embolic agents from migrating are described. The concept has particular benefit in allowing liquid embolic to be used with a variety of intravascular therapeutic applications, including for occluding aneurysms and arteriovenous malformations in the neurovasculature.

20 Claims, 24 Drawing Sheets

(56) References Cited

U.S. PATENT DOCUMENTS

| | | |
|---|---|---|
| 2003/0093108 A1 | 5/2003 | Avellanet et al. |
| 2003/0181927 A1 | 9/2003 | Wallace |
| 2003/0187473 A1 | 10/2003 | Berenstein et al. |
| 2003/0195553 A1 | 10/2003 | Wallace et al. |
| 2004/0122455 A1 | 6/2004 | Lin |
| 2006/0064151 A1 | 3/2006 | Guterman et al. |
| 2008/0045995 A1 | 2/2008 | Guterman et al. |
| 2008/0140177 A1 | 6/2008 | Hines |
| 2008/0161936 A1 | 7/2008 | Feller et al. |
| 2011/0264132 A1 | 10/2011 | Strauss et al. |
| 2013/0245745 A1 | 9/2013 | Vong et al. |
| 2014/0046359 A1 | 2/2014 | Bowman et al. |
| 2014/0135812 A1* | 5/2014 | Divino ............ A61B 17/12113 606/194 |
| 2014/0200607 A1 | 7/2014 | Sepetka et al. |
| 2014/0288588 A1 | 9/2014 | Lam et al. |
| 2015/0133994 A1 | 5/2015 | Amplatz et al. |
| 2015/0173919 A1 | 6/2015 | Baldwin |
| 2016/0199204 A1 | 7/2016 | Pung et al. |
| 2016/0242893 A1 | 8/2016 | Joshi et al. |
| 2016/0331379 A1 | 11/2016 | Furey et al. |
| 2017/0367713 A1* | 12/2017 | Greene, Jr. ...... A61B 17/12031 |

* cited by examiner

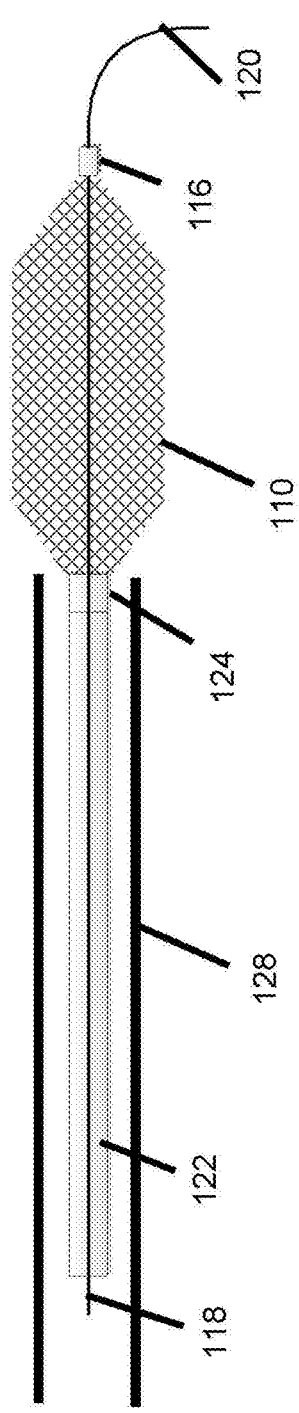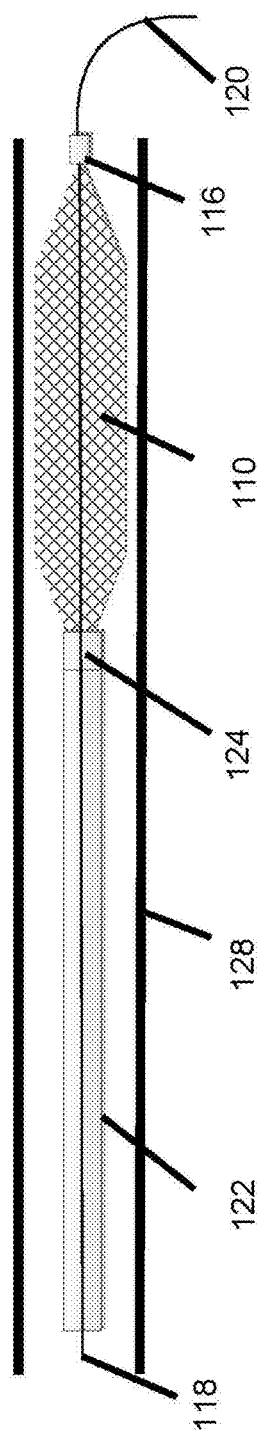
Figure 3
Figure 4

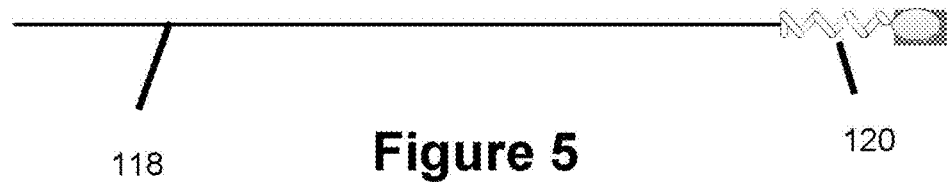
118    Figure 5    120
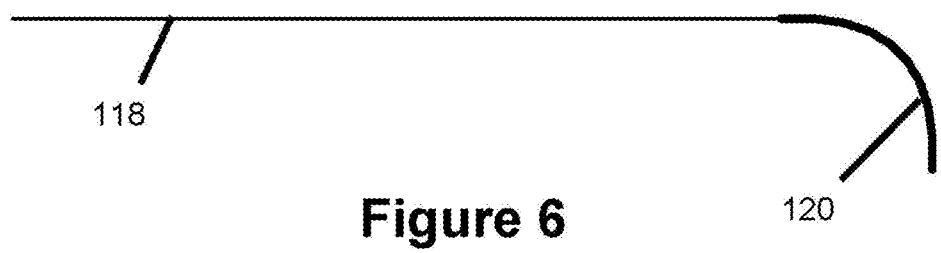
118    Figure 6    120
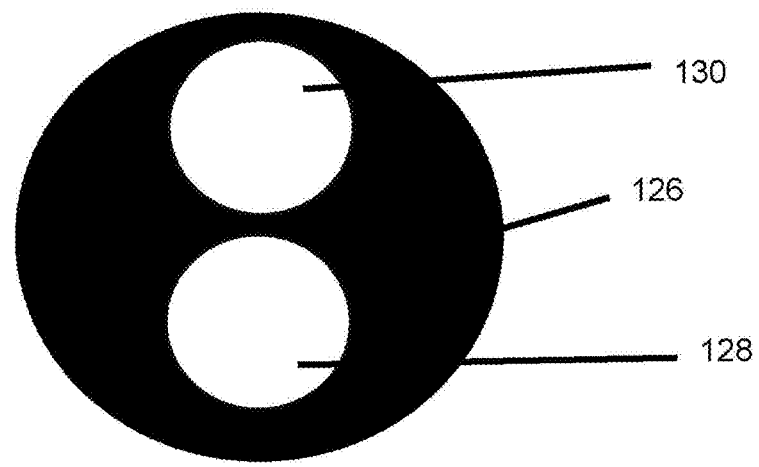
Figure 7

EMBOLIC CONTAINMENT

RELATED APPLICATIONS

This application is a continuation-in-part of U.S. patent application Ser. No. 15/599,284 filed May 18, 2017 entitled Embolic Containment, which in turn claims priority to U.S. Provisional Application Ser. No. 62/338,387 filed May 18, 2016 entitled Embolic Shield, U.S. Provisional Application Ser. No. 62/338,395 filed May 18, 2016 entitled Embolic Shield System, and U.S. Provisional Application Ser. No. 62/338,405 filed May 18, 2016 entitled Intrasaccular Embolic Shield, all of which are hereby incorporated herein by reference in their entirety.

FIELD OF THE INVENTION

The invention deals with the area of intravascular therapeutic treatment and the use of medical devices and occlusive or embolic material to treat a vascular condition.

BACKGROUND OF THE INVENTION

Embolic agents, including embolic coils, embolic meshes, and liquid embolic among other agents are often used to occlude a target site within the vasculature to treat a variety of conditions. A non-exhaustive list of conditions includes aneurysms, atrial septal defects, patent foramen ovale, left atrial appendage occlusion, patent ductus arteriosus, fistula, arterio-venous malformations, fallopian tube occlusion for the purposes of sterilization, spermatic vein occlusion to test infertility, and occlusion in the peripheral vasculature.

Liquid embolic is part of a newer class of compounds and are a type of biocompatible liquid which precipitates upon exposure to blood to harden and occlude a treatment site. Liquid embolic, while offering some occlusive advantages, can be difficult to use since there is a high risk of the liquid embolic migrating out of the treatment site. Therefore, currently liquid embolic can only be used for a few vascular conditions. The following embodiments deal with devices, systems, and methods to seal a treatment site and prevent liquid embolic migration after delivery. The embodiments have particular utility in containing the migration of liquid embolic, therefore allowing liquid embolic to be used to treat a host of vascular conditions, including aneurysms and arteriovenous malformations.

SUMMARY OF THE INVENTION

The invention involves various ways of dealing with the issue of liquid embolic migration during vascular treatment, thus allowing liquid embolic to be used to treat a variety of conditions, including conditions where liquid embolic currently cannot be used due to the risk of embolic migration.

In some embodiments, a sealing device/system which is particularly useful in treating sidewall aneurysms is described. The sealing device/system is used to seal a target treatment site, helping to keep liquid embolic within a treatment area and preventing liquid embolic from migrating out of the treatment area. The sealing device/system has particular usefulness in keeping liquid embolic within an aneurysm, such as a sidewall aneurysm, to occlude the aneurysm.

In one embodiment, a sealing device comprises a multiple layer structure. The multiple layers can extend through the entirety of the sealing device, or alternatively can extend through just a portion of the sealing device. In one embodiment, the sealing device comprises a dual layer mesh—in one embodiment, the dual layer mesh includes a looser outer layer and a denser inner layer, this configuration is particularly useful for trapping liquid embolic in between the two layers. In another embodiment, the sealing device includes a multiple layer structure wherein one of the layers comprises a stent. In one embodiment, the sealing device comprises a first layer that forms the length of the device, and a second layer that extends through the middle of the device. Each mesh may have different porosity or cell size, and the meshes may expand or collapse independently of each other. In one embodiment, the sealing device comprises an inner balloon and an outer mesh layer. The various layers can be attached together or in other embodiments can be completely independent of each other.

In one embodiment, the sealing device has a cylindrical medial section configured to face the neck of an aneurysm and tapered proximal and distal end sections. In one embodiment, the tapered proximal and distal ends have a conical shape. In one embodiment, the tapered distal end has a rounded shape. In one embodiment, the cylindrical medial section includes both an inner and outer layer where the inner layer is denser than the outer layer, this configuration is particularly useful for trapping liquid embolic in between the two layers. In one embodiment the inner layer is present throughout the sealing device, in another embodiment the inner layer is present through just the proximal and medial sections of the device, and in another embodiment the inner layer is present through just the medial and distal sections of the device. The inner layer can be used in the distal region of the device to form a catch structure to aid in retaining embolic.

The sealing device is delivered by a pusher. In one embodiment, the pusher is a tube and includes a core wire which spans both the pusher and the sealing device. In one embodiment, the core wire can function like a guidewire and can be used to track a catheter and the sealing device. In one embodiment the core wire is completely fixed, in another embodiment the core wire has complete freedom of movement, in another embodiment the core wire has some limited freedom of movement—for example, the core wire can move freely distally but has limited movement in a proximal direction. In some embodiments, the core wire can be configured so that pushing and/or pulling the core wire can affect the radial expansion/contraction of the sealing device. This property can be used to increase the radial expansion of the sealing device to aid in completely sealing the treatment site and preventing liquid embolic from leaking past the treatment site.

In one embodiment, a sealing system is described which has particular usefulness in sealing liquid embolic within a sidewall aneurysm. The system includes an expandable structure delivered by a pusher, where the pusher includes a lumen which accommodates a core wire. The core wire spans both the pusher and the expandable structure. In some embodiments, the core wire is configured so that pushing and/or pulling the core wire can lengthen and/or contract the expandable structure. In some embodiments, the expandable structure is a mesh device where some parts of the device have both an inner and outer mesh layer, where the inner layer is denser than the outer layer such that the space in between the two layers can be used to trap embolic.

In one embodiment, a method of treating a vascular condition includes placing a first catheter connected to a liquid embolic source within a vascular condition. A sealing device or system, which comprises an expandable structure and a pusher with a lumen therein which delivers the expandable structure, is then placed flush with the neck or opening of the vascular condition—in one embodiment, the expandable structure includes a cylindrical medial section and this medial section is placed flush with the neck or opening of the vascular condition. The lumen accommodates a wire which also spans the expandable structure, where the wire can be manipulated in order to control the shape of the expandable structure so that the expandable structure can be configured to sit flush with opening of the vascular condition. In one embodiment, the expandable structure includes a porous outer layer and dense inner layer. Liquid embolic is delivered through the catheter placed within the vascular condition, and the expandable structure prevents migration of the liquid embolic, where the liquid embolic is trapped between the inner and outer layers of the expandable structure. In one embodiment, the vascular condition treated in an aneurysm. In one embodiment, the vascular condition treated is a sidewall aneurysm.

In some embodiments, a sealing device/system, which is particularly useful in treating bifurcation aneurysms, is described. The sealing device/system has particular usefulness in keeping liquid embolic within an aneurysm, such as a bifurcation aneurysm, to occlude the aneurysm.

In one embodiment, a sealing device includes an occluder where the occluder is an intrasaccular agent which sits completely within the treatment site. In another embodiment, the occluder is a neck seal which sits at the neck of the treatment site—where either a portion of the occluder can sit within the treatment site, or all of the occluder can sit outside of the treatment site. In one embodiment, the occluder includes a first region and a second region where the regions are separated by a narrowed section. In one embodiment, the occluder includes foldable layers. In one embodiment, the occluder is comprised of a mesh of wires. In one embodiment, the occluder includes a polymeric coating.

A tension wire is pushed and pulled to lengthen and compress the shape of the occluder. In one embodiment, the tension wire is selectively removable from the occluder. In one embodiment, the tension wire is selectively removable from the occluder via a threaded mechanical connection. The occluder is delivered by a pusher. In one embodiment, the occluder is connected to the distal part a pusher and is detachable from the pusher so that after detachment, the pusher lumen can subsequently be used to deliver additional embolic agents, including liquid embolic.

In one embodiment, a sealing device includes an occluder with a coiled element connected to a distal portion of the occluder. The tension wire connects to the coiled element. In one embodiment, the tension wire is selectively removable from the coiled element. In one embodiment, the tension wire is selectively removable from the coiled element via a threaded mechanical connection.

In one embodiment, a sealing system which has particular usefulness in sealing liquid embolic within a bifurcation aneurysm includes an occluder, a pusher used to push the occluder, and a tension wire spanning both pusher and the occluder. The tension wire can be manipulated in order to compress and lengthen the occluder. The tension wire is removable from the occluder and pusher. Once the tension wire is removed, the pusher can be used to deliver additional embolic agents, including liquid embolic, through the occluder. In one embodiment, the occluder is detachable from the pusher.

In one embodiment, a method of treating a vascular condition includes delivering a sealing device or system—which comprises an occluder, tension wire, and pusher tube—where a portion, or all of the occluder sits outside the vascular condition. A tension wire spans the pusher and occluder and is used to control the shape of the occluder. The tension wire is optionally removed from the occluder and withdrawn through the pusher. The pusher is subsequently used to deliver a liquid embolic. In one embodiment, the vascular condition treated is a bifurcation aneurysm.

In some embodiments, a sealing device/system which is particularly useful in treating arteriovenous malformations (AVM's) is described. The sealing device has particular usefulness in keeping liquid embolic within an AVM, to occlude the AVM.

In one embodiment, a sealing device comprising a catheter and a catch or shield structure placed on a distal region of a catheter is described. In one embodiment, the catch comprises a mesh or braid comprised of wires. In one embodiment, the catch is detachable. In one embodiment, a detachment system for detaching a catch is described.

A method of embolic delivery is described in some embodiments. A catheter connected to a liquid embolic source is navigated through the venous side of the vasculature, to the location of an AVM. The proximal section of the catheter includes a port for liquid embolic injection. The distal region of the catheter includes a catch and a lumen for liquid embolic delivery. Liquid embolic is delivered through the catheter into the AVM, and the catch ensures any liquid embolic backflow is caught so that liquid embolic does not collect in the venous side of the vasculature. In one embodiment, the catch is optionally detachable from the catheter, where a detachment sequence may be initiated to detach the catch.

A method of embolic delivery utilizing two catheters is described in some embodiments. A first catheter is connected to a liquid embolic source and is navigated through the arterial side of the vasculature to the location of an AVM. A second catheter includes a distal catch and is navigated through the venous side of the vasculature near the location of an AVM. The first catheter delivers liquid embolic from the arterial side of the AVM, and the second catheter's catch structure is used to catch any liquid embolic that flows through the AVM to the venous system. The second catheter therefore operates as a catch, ensuring liquid embolic delivered from the arterial side of the AVM does not end up in the venous system. In one embodiment, both catheters are used to deliver liquid embolic so that the AVM is occluded from both the arterial side and the venous side, and the second catheter's catch on the venous side of the AVM ensures no liquid embolic migrates in the venous system of the vasculature.

An AVM treatment procedure is described in some embodiments. In one embodiment, a catheter is tracked through the venous system of the vasculature, to a point near an AVM. The catheter includes a catch on the distal region of the catheter. Liquid embolic is delivered through the catheter into the AVM to occlude the AVM. Any embolic backflow is caught by the catch. In one embodiment, the catch is optionally detachable from the catheter. Once the AVM is occluded, normal blood flow through the artery, capillaries, and veins is preserved.

In another embodiment, an AVM treatment procedure utilizes two catheters—a first catheter is connected to a liquid embolic source and a second catheter contains a distal catch. The first catheter is tracked through the arterial system to the location of an AVM. The second catheter is tracked through the venous system and is tracked to the location of an AVM, such that the first and second catheters are on opposite sides of the AVM. Liquid embolic is delivered through the first catheter such that the AVM is occluded with liquid embolic from the arterial side of the AVM. The catch on the second catheter, which sits on the venous side of the AVM, catches any embolic which migrates from the AVM ensuring that liquid embolic does not end up in the venous system. In one embodiment, both catheters are connected to liquid embolic sources and are used to deliver liquid embolic so that the AVM is occluded from both the arterial side and the venous side, and the second catheter's catch on the venous side of the AVM ensures no liquid embolic migrates in the venous system of the vasculature.

A catheter is described in some embodiments. In one embodiment, the catheter comprises a catch located at the distal portion of the catheter. In one embodiment, the catch is detachable from the catheter and the catheter includes a detachment system which is optionally used to detach the catch. In one embodiment, the catheter is used for liquid embolic injection to treat AVM's.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which:

FIG. 3 illustrates a pusher delivery system used with a sealing device where the sealing device is in an expanded configuration, according to one embodiment.

FIG. 4 illustrates a pusher delivery system used with a sealing device where the sealing device is in a collapsed configuration, according to one embodiment.

FIG. 5 illustrates a core wire with a coiled distal tip used with a sealing device, according to one embodiment.

FIG. 6 illustrates a core wire with a bent distal tip used with a sealing device, according to one embodiment.

FIG. 7 illustrates a cross-section of a guide or access catheter used to deliver a sealing device and embolic agent, according to one embodiment.

DESCRIPTION OF EMBODIMENTS

Figure 1:
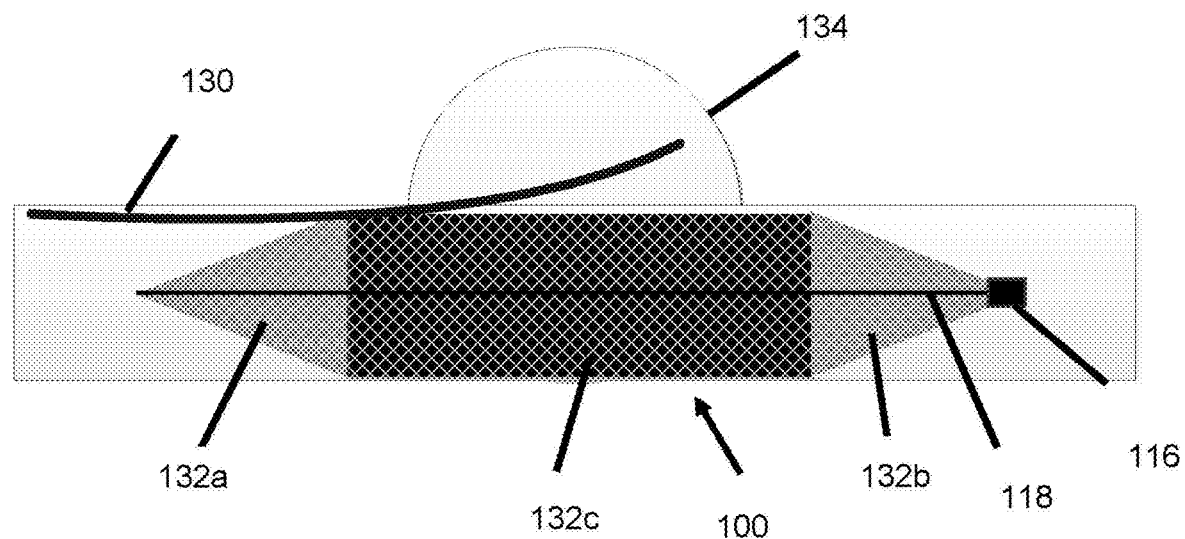
FIG. 1 illustrates a sealing device used to treat an aneurysm, according to one embodiment.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Occlusion or embolization is a technique used to treat a variety of intravascular conditions, such as aneurysms, atrial septal defects, patent foramen ovale, left atrial appendage occlusion, patent ductus arteriosus, fistula, arterio-venous malformations (AVM), fallopian tube occlusion for the purposes of sterilization, spermatic vein occlusion to test infertility, and occlusion in the peripheral vasculature. To promote occlusion, embolic material such as embolic coils or embolic meshes are used to fill the treatment site (e.g. aneurysm), which over time cuts off blood flow to the site, promotes clotting, and—in the case of aneurysms—helps prevent vessel rupture which could otherwise lead to stroke.

Liquid embolic is part of a newer class of embolic agents. Some liquid embolic embodiments are described in U.S. Pat. No. 9,078,950, which is hereby incorporated by reference in its entirety. Liquid embolic is a viscous biocompatible liquid. The liquid embolic precipitates after exposure to blood or aqueous solutions. Many varieties of liquid embolic are mixed with dimethyl sulfoxide (DMSO) solvent to prevent early solidification. Upon delivery through the delivery catheter and into the treatment site, the DMSO will rapidly diffuse away causing the embolic material to precipitate due to exposure to blood. The precipitated embolic will occlude the treatment site, preventing blood flow into the target area. Liquid embolic is currently used to treat AVM's, however, using liquid embolic to treat other vascular conditions such as aneurysms is difficult since the embolic can migrate to other areas of the vasculature prior to solidifying, or can solidify and still migrate to other areas of the vasculature. Stents cannot be used to seal the aneurysm treatment area since stent pore sizes are too large to prevent outflow of liquid embolic and the open ends of the stent provide an easy escape path for embolic. Additionally, even when liquid embolic is used to treat AVM's there is still a risk of embolic migration.

The present invention addresses the issues associated with liquid embolic migration by providing a sealing device/system that sufficiently seals a target treatment site to prevent migration of embolic material—thereby allowing liquid embolic to be used in a variety of therapeutic procedures, such as treating aneurysms, where it currently cannot be used due to the risk of embolic migration.

For the purposes of illustrative ease, the sealing device, systems, and methods going forward will be described primarily in the treatment of aneurysms and AVM's. Though the following embodiments have particular utility when used with aneurysms and/or AVM's they are not limited to this application and can be used to treat a variety of conditions/vascular malformations including aneurysms, atrial septal defects, patent foramen ovale, left atrial appendage occlusion, patent ductus arteriosus, fistula, arterio-venous malformations, fallopian tube occlusion or spermatic vein occlusion for the purposes of sterilization, and occlusion in the peripheral vasculature.

The following embodiments shown in FIGS. 1-9 and described below have particular usefulness in treating aneurysms, including sidewall aneurysms. Aneurysms occur when there is a weakened region along the wall of a blood vessel; this weakened region develops into a protruding bulge which can eventually rupture leading to complications such as stroke when these aneurysms occur in the neurovasculature. Sidewall aneurysms occur along the sidewall of a blood vessel. Liquid embolic generally cannot be used to treat sidewall aneurysms due to the high risk of liquid embolic migration prior to solidification or even after solidification, where the liquid embolic can migrate elsewhere leading to major complications. The following embodiments are geared towards a sealing device that is placed against the opening of the aneurysm to contain liquid embolic within the aneurysm.

Stents are sometimes used to treat aneurysms, where the stent is an open ended tubular structure placed across the neck of the aneurysm. Flow diversion stents are stents with relatively small pore sizes, where the smaller pore sizes limit blood flow to the aneurysm closing off access to the aneurysm over time. Assist stents are also used, and these assist stents include pores and a microcatheter is placed within the stent pores to deliver embolic coils into the aneurysm to occlude the aneurysm in a procedure known as stent assisted coil embolization. Neither type of stent can be used with liquid embolic delivery for a variety of reasons. First, the proximal and distal open ends of a stent provide an easy escape path for liquid embolic which might seep through the stent, heightening the risk of occlusion and stroke elsewhere in the vasculature based on migration of the embolic formation. Second, assist-stents include large pores in order to accommodate a microcatheter which is delivered through the pores—these pores are too large to prevent the passage of liquid embolic material.

FIG. 1 shows a sealing device 100 according to one embodiment, and in particular illustrates how the sealing device 100 would be positioned relative to an aneurysm 134, in this case a sidewall aneurysm. Microcatheter 130 is positioned within the aneurysm to deliver liquid embolic and sealing device 100 is placed to block the neck of the aneurysm. Sealing device 100 prevents the delivered embolic material from migrating from aneurysm 134. In one embodiment, sealing device 100 generally has a cylindrical center section 132c and tapered end sections 132a and 132b. The tapered end sections provide a generally closed proximal and distal end section, which helps to prevent the passage of liquid embolic where liquid embolic migrates through the sealing device. Please note, the term taper refers to involving a diameter reduction in a particular direction. For the purposes of FIG. 1, the particular shape shown is conical type of taper, though other tapered shapes are also possible. Cylindrical center section 132c can be thought of as representing the working length of the device since, as shown in FIG. 1, this section will sit in the blood vessel over the neck of the aneurysm to help seal the neck of the aneurysm and prevent embolic discharge from the aneurysm.

Sealing device 100 is expandable, adopting a collapsed shape during delivery through a catheter and an expanded shape once delivered from the catheter. In this way, sealing device 100 can be thought of as an expandable structure. Sealing device 100 includes a core wire 118 spanning the sealing device, as will be explained in more detail later. Core wire 118 is used to manipulate the shape of the sealing device 100 such that retracting the core wire causes the sealing device 100 to radially expand and therefore help seal a treatment area. In this manner, core wire 118 can be thought of as a controller, more specifically an expandable structure controller, where the core wire can be used to control the shape of the expandable structure sealing device in order to allow the sealing device to adopt an optimal shape to seal a treatment area and prevent liquid embolic discharge out of the vascular treatment site.

As mentioned earlier, several types of liquid embolic are delivered along with DMSO to keep the liquid embolic from prematurely precipitating and solidifying. The liquid embolic solidifies once exposed to blood, and the DMSO which is delivered along with the liquid embolic dissipates through the bloodstream. Sealing device 100 acts as a restraining agent to help keep the liquid embolic in aneurysm 134 and keep liquid embolic from migrating elsewhere in the vasculature—for example, in scenarios where the liquid embolic does not immediately precipitate and a portion of it may migrate out of the aneurysm before solidification, or in scenarios where a portion of the precipitated liquid embolic may migrate out of the aneurysm.

Figure 2:
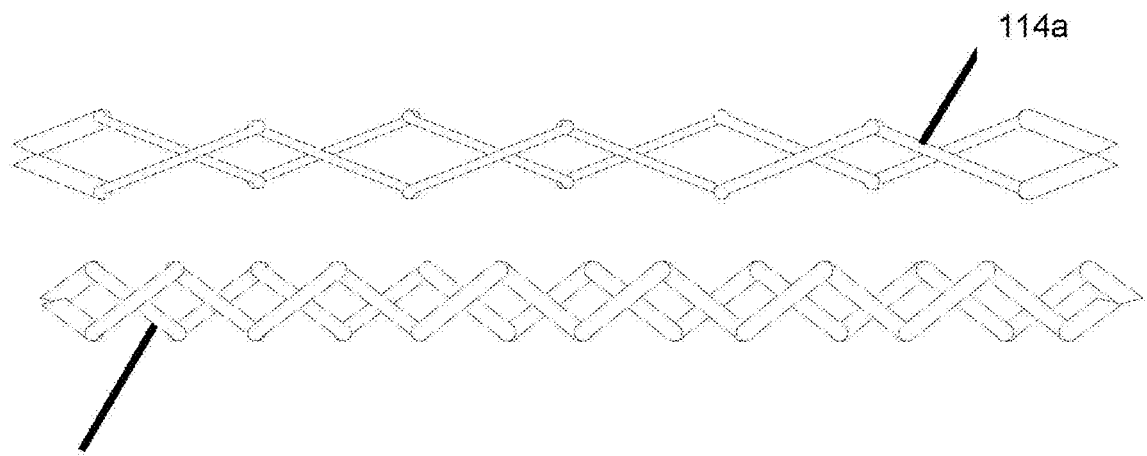
FIG. 2 illustrates an inner and an outer mesh of a sealing device, according to one embodiment.

In one embodiment, the sealing device 110 comprises two layers—an inner layer 112a and outer layer 114a as shown in FIG. 2. In one embodiment, the inner and outer layer are both meshes comprised of metallic wires. The metallic wire mesh can include some nitinol and some radiopaque (e.g. tantalum, platinum, gold) wires, the inclusion of radiopaque wires will aid in visualization. Alternatively, the wires can comprise a nitinol core with a radiopaque exterior, or a radiopaque core with a nitinol exterior. Alternatively, one of the mesh layers can include solely nitinol wires while the other mesh layer includes both nitinol and radiopaque wires. In one embodiment, the inner layer 112a mesh and/or outer layer 114a mesh could be comprised of drawn-filled tubing (DFT). DFT utilizes an inner core material surrounded by an outer jacket and is described in U.S. Pat. No. 7,420,124 which is hereby incorporated by reference in its entirety. The inner core can comprise one or more wire elements. By using different materials for the inner layer and outer jacket, it is possible to create a mesh utilizing different material properties. In one embodiment, DFT utilizing a platinum inner core and a nitinol outer jacket is used. The platinum inner core would augment radiopacity and aid in visualizing the device while the nitinol outer jacket would provide good shape memory retention. The sealing device should have a good amount of shape memory, which a nitinol wire-based device should have due to the strong shape-memory properties of nitinol. Known heat treatments to impart shape memory, such as heat treatment over a mandrel shaped to the shape of the sealing device, can be used to impart this shape memory. The shape memory would mean the sealing device 110 could adopt a collapsed shape when housed within a microcatheter, and then an expanded shape upon release from the microcatheter due to the imparted shape memory. The sealing device can therefore be thought of as an expandable structure which adopts a collapsed configuration when housed in a microcatheter, and an expanded configuration when freed from said microcatheter.

In one embodiment, inner layer 112a and outer layer 114a are attached together. Mechanical ties can be selectively placed throughout the length of both layers to attach the layers to each other. Alternatively, a wire can be woven with the two layers in an alternating pattern (e.g. below the bottom layer, above the top layer, below the bottom layer, above the top layer, etc.) in order to bind the layers together. In another embodiment, no attachment means are used between the layers—instead, each layer is formed of shape memory material and the built-in shape memory of the layers will allow each layer to expand once the sealing device is pushed out from the delivery catheter. The amount of built-in shape memory and size of the blood vessel, would inherently control the expansion of both layers. Known heat treatments to impart shape memory, such as heat treatment over a mandrel shaped to the shape of the sealing device, can be used to impart this shape memory. Nitinol has a particularly good shape memory quality, so the layers could include at least some nitinol wires in the mesh to impart strong shape memory within the layers of the sealing device.

In one preferred embodiment, the inner layer 112a is comprised of a denser mesh than the outer layer 114a. Where the sealing device is used to retain liquid embolic material delivered through a microcatheter 130 (as shown in FIG. 1), the looser outer layer might allow some liquid embolic through, but the denser inner mesh would catch the liquid embolic and prevent it from permeating through the inner mesh. This embodiment would be made by using a mandrel to braid a dense mesh, and using a mandrel to braid a looser outer mesh. The looser outer mesh would be placed over the denser, inner mesh. Optional attachments, as discussed above, could be subsequently used to bind the layers. Since the sealing device does not need to accommodate a microcatheter, inner layer 112a can be particularly dense to help prevent the passage of liquid embolic through the inner layer and through the sealing device. As a failsafe, the tapered proximal and distal ends 132a, 132b of the sealing device provide a catch structure to catch any displaced liquid embolic.

In one embodiment, the looser outer layer comprises the length of the device, and the denser inner layer sits within solely the middle section of the device. The middle section 132b sits against the entrance to the aneurysm as shown in FIG. 1, the denser inner braid of the device will therefore be aligned with the neck of the aneurysm and catch any loose or migrating embolic from the aneurysm. Meanwhile, the proximal and distal ends 132a, 132b of the device comprise solely the looser outer mesh—and not the denser inner mesh—to enable blood and DMSO to flow unperturbed through these regions of the sealing device.

In another embodiment, the looser outer layer is used along the complete length of the device and the middle 132c and distal 132b sections of the device utilize a dense inner layer. This may be preferable to help ensure liquid embolic cannot migrate distally—as the dense distal end of the device would act like a catch if embolic happened to seep through the inner layer. Since these devices are typically placed in the direction of blood flow, one can imagine blood flowing left to right and the device being placed so that the proximal end 132a is to the left and the distal end 132b is to the right. Since blood flows toward the 'right' or distal side, having the catch on the distal or 'right' side is preferable since the embolic could migrate downstream. In this embodiment, any liquid embolic making it past the dense inner layer 112a of the middle section 132c of the device would encounter another dense inner layer 112a and a looser outer layer at distal tapered region 132b. Even in situations where the inner layer is not used on the distal tapered section 132b of the device, the device can easily be configured so that the distal tapered section 132b is denser than other sections of the device—in other words, the outer layer 114a can be designed so that the outer layer at the distal tapered section 132b is less porous than the outer layer in the medial section 132c of the device.

In one embodiment, the denser inner mesh will prevent the liquid embolic agent from entering, trapping the liquid embolic between the inner and outer layer and forming a thin film between the two layers, which will allow the inner layer to collapse to aid in retrieval. Since DMSO is less viscous than pre-precipitated liquid embolic (and certainly less viscous than solidified or precipitated liquid embolic), a denser distal tapered end 132b should not impact the ability of DMSO and blood to flow through this region since DMSO and blood are substantially less viscous than liquid embolic.

Other embodiments could utilize additional layers, for instance three or more layers where the mesh density profile of each layer could vary from the other layers. Other embodiments could utilize a sealing device comprising polymers instead of a metallic mesh structure. Other embodiments could utilize a combination of polymers and metallic meshes use to create the sealing device. Other embodiments could utilize a solid multi-layer tubular structure which is laser-cut to create pores on each layer. Other embodiments could utilize a stent as the inner layer, where a mesh with tapered proximal and distal sections is placed over the stent to create a multi-layer structure.

In one embodiment, the cylindrical medial section/working length portion of the device 132c can utilize radiopaque components to aid in visualization so the user can tell where the working length of the device is placed relative to the aneurysm. In one example, radiopaque marker coils or marker bands made of platinum, tantalum, or gold can be selectively placed throughout section 132c of the device so this section of the device is particularly visible.

The sealing device includes a distal marker 116 shown in FIGS. 1 and 3-4, which is a radiopaque marker band comprising a radiopaque substance such as gold, tantalum, platinum, or palladium that can be used to crimp the distal end of the outer layer mesh. A marker band (not shown) could also be used at the proximal end of the device to crimp the proximal end of the outer layer mesh. The marker band would include a lumen; the marker band could therefore be thought of as a hollow cylinder or tube. The radiopaque marker would be useful for imaging purposes to visualize the ends of the device to aid in placement of the sealing device relative to the vascular condition. A core wire 118 spans the length of the device and also spans a hypotube delivery pusher 122 proximally connected to the sealing device 110 which is used to deliver (push/pull) the sealing device 110 through a catheter—as shown in FIGS. 3-4. Core wire 118 sits through the marker band lumen. Core wire 118 can be made of a variety of materials, such as a metallic (e.g. nitinol or stainless steel) wire or hypotube; alternatively a radiopaque substance such a tantalum, platinum, gold, or tungsten can be used. In one embodiment, core wire 118 is made of a nitinol wire which is wrapped with a radiopaque coiled wire to aid in visualizing the core wire. The delivery system and method of delivery utilizing core wire 118 will be discussed in more detail later.

FIGS. 3-4 show the delivery system for the sealing device, according to one embodiment. Sealing device 110 is connected to the distal end of a hypotube pusher 122. The pusher is controlled from the proximal end of the system by the user to push and pull both the hypotube 122 and the attached sealing device 110 through a microcatheter 128 and through the vasculature. The hypotube pusher is a tube and includes an interior channel or lumen. Core wire 118 sits within this channel and runs from the proximal end to the system—where it is manipulated by the user similar to a guidewire to track the guidewire and catheter through the vasculature—to the distal end of the system where it sits distal of the sealing device. The proximal portion of the sealing device 110 is affixed to the distal end of hypotube 122. In one example, the proximal portion of the sealing device 110 is affixed via welding, adhesive, or similar means to the interior of the hypotube at location 124—though the proximal end of sealing device 110 could also be affixed to the outside of the hypotube at location 124. In one embodiment, there are no detachment means to detach the sealing device from the hypotube. Since the sealing device is meant to be used just to prevent embolic migration from the aneurysm, once the liquid embolic is injected within the aneurysm and the embolic precipitates to occlude the aneurysm, the sealing device is removed from the vasculature. This can be accomplished by retracting the hypotube pusher proximally through microcatheter 128, which is also used to deliver the sealing device. However, in alternative embodiments, it would be easy to introduce a detachment system at the distal part of the hypotube pusher to detach the sealing device—electrolytic, mechanical, or thermal means could be used. In one example there is a sacrificial element between the sealing device and hypotube (e.g. at location 124 of FIGS. 3-4) that is thermally, electrolytically, or mechanically degraded in order to detach the sealing device. US20100269204, US20110301686, US20150289879 all describe thermal detachment systems and are hereby incorporated by reference in their entirety.

FIGS. 5-6 show two embodiments of the core wire 118 which spans the length of the sealing device. FIG. 5 shows the core wire 118 culminating in a distal coiled tip 120 which passes through the lumen of distal marker 116 and sits distal of marker 116. The coiled tip is comprised of a coil; a coil shape is useful since if the distal tip hits a vessel, the coiled tip allows for some flexibility which reduces the likelihood that the tip will get stuck or stab into the vessel wall. FIG. 6 shows the core wire 118 culminating in a bent tip 120. Bent tip 120 is more malleable than the rest of the core wire and is meant to be bent in any direction. The user would pre-shape the distal tip by bending it physically, or using a mandrel or tool to bend the distal tip in a particular direction. This bent shape is desirable so that if the wire is being navigated through the vasculature and there is a bifurcation, the user can rotate the wire so that the bent tip aligns with the correct vessel, and the wire can then be pushed through the appropriate vessel. This bent shape configuration, known as a J-shape in the art, if often used on guidewires to aid in tracking a guidewire through tortuous anatomy, particularly at bifurcations where a user must be able to select a particular vessel—the user will rotate or manipulate the guidewire into the desired vessel at a bifurcation point and then continue to track the guidewire.

Generally in order to access a vascular treatment site, a guidewire is first introduced into the vasculature and large-lumen guide or access catheter is tracked over the guidewire to access the treatment site. The guide or access catheter provides an access path for a smaller microcatheter which is used to deliver a medical device or therapeutic material to the target region. The guidewire is a thin, navigable wire used solely to access a target region, and the guidewire is withdrawn once the target region is accessed. The inclusion of core wire 118 which spans the sealing device would allow the core wire, in essence, to function like a guidewire and be used to track the catheter to the treatment site—in a manner that will now be described.

In one embodiment, the core wire 118 and core wire distal tip 120 (see FIGS. 3-6) is freely moveable, such that the core wire 118 is not affixed to anything and is freely moveable through sealing device 110 and can even be completely removed by pulling the core wire 118 to retract it through the sealing device 110 and completely out of the vasculature if so desired by retracting the core wire completely. In practical terms, this means the lumen within marker band 116 would be larger than the core wire 118 diameter and core wire distal tip 120 diameter. Core wire 118 could function as a guidewire since the core wire 118 could be pushed far distally of the sealing device 110 and then used to track the sealing device and catheter 128.

In another embodiment, the core wire 118 could be freely movable distally but distal tip 120 is larger than the marker band 116 lumen so that the distal tip 120 is not retractable through the sealing device 110. In practical terms, this means the core wire distal section 120 is thicker than the rest of core wire 118 and is also thicker than the distal marker 116 lumen and would therefore contact the distal marker 116 upon retraction, limiting the amount of proximal movement of the core wire. Allowing some free distal mobility of the core wire distal section 120 would allow for configurations like the one described above, where the core wire 118 could function like a guidewire and where the core wire 118 could be used to track the sealing device 110 and microcatheter 128. Since the core wire 118 is distally pushable, the user could simply push the core wire 118 so that the distal tip 120 of the core wire sits far beyond the distal end of the sealing device 110 and far beyond the distal end of the catheter 124 that the sealing device 110 is delivered through. The sealing device 110 and catheter 124 could then be tracked over the core wire 118. Retracting core wire 118 would cause core wire distal tip 120 to contact marker band 116, applying a sufficient retraction force on core wire 118 would cause sealing device 110 to radially expand and longitudinally contract due to the force exerted by distal tip 120 on marker band 116 and sealing device 110. The ability to control the radial shape of the sealing device in this manner will be appreciated later.

In another embodiment, the core wire distal tip 120 is not freely movable and adopts a fixed position. In one embodiment, the core wire distal tip 120 is in a fixed position far distal of the sealing device and the sealing device, as it contracts and expands (e.g., during delivery), can float over the fixed core wire—so that the sealing device can be pushed over the fixed core wire via the pusher 122. In one embodiment, a tightening mechanism such as a collet can be used to selectively lock core wire 118 in a fixed position—this collet would sit at a proximal location, such that a user could tighten the collet to lock the core wire 118 or loosen the collet to move the core wire 118. In one embodiment, this fixed position is achieved by affixing core wire 118 or the core wire distal tip 120 directly to distal marker 116 so that core wire 118 is fixed and not freely movable; this can be done via welding or adhesives. In one example, core wire 118 is welded or adhesively affixed to the interior or exterior of the marker band 116. In another example, core wire distal tip 120 is thicker than the rest of core wire 118 and the distal tip 120 is mechanically affixed (via adhesive or welding) to distal marker band 116. One advantage of the system where the core wire is affixed to distal marker 116 is that pulling on core wire 118 will pull the distal marker 116 proximally since the core wire and marker are connected, thereby radially expanding the shape of the sealing device—this happens since the sealing device is linked to the hypotube at one end and to the distal marker and the core wire at the other end. Similarly, pushing on the core wire will elongate the sealing device and cause it to adopt a more elongate, less radially full profile. The ability to control the radial shape of the sealing device in this manner will be appreciated later. Where a fixed core wire 118 configuration is used, the portion of core wire 118 sitting within cylindrical medial section 132c of the device can utilize a radiopaque component (e.g. the radiopaque coiled wire surrounding a nitinol wire discussed earlier) to aid in visualizing cylindrical section 132c of the device.

Referencing FIG. 1, a microcatheter 130 used to deliver liquid embolic is placed within the aneurysm 134 and a sealing device 100 is subsequently placed to seal the aneurysm. The sealing device is delivered through a separate microcatheter 128, as shown in FIGS. 3-4. Because multiple microcatheters are needed (one microcatheter to deliver the sealing device, and another to deliver the liquid embolic), delivery of two separate microcatheters can be an issue given the time needed to track two separate microcatheters through the vasculature. In one embodiment, both microcatheters 128 and 130 are placed through a larger lumen guide or access catheter 126—as shown in FIG. 7. This configuration can be achieved in a number of different ways. For example, the larger delivery catheter 126 can include two lumens, and these individual lumens provide access for microcatheters 128, 130. Alternatively, the larger delivery catheter has a single lumen and microcatheters 128, 130 are both placed within this lumen. Alternatively still, the larger delivery catheter 126 contains two lumens and one of these lumens is used to deliver embolic and the other lumen is used to deliver the sealing device (in essence, the open lumens themselves would act like microcatheters). For illustration, the guide or access catheter 126 can be 6 or 7 French size (about 2-2⅓ mm outer diameter), while microcatheters 128, 130 are 2 or 3 French size (about ⅔-1 mm outer diameter). For inner diameter illustration, microcatheters 128 and 130 can have an inner diameter of 0.017, 0.021, or 0.027 inches. These sizes are purely for illustration and the sizes of the microcatheters and delivery catheter can be sized up or sized down as needed.

A separate guidewire can be used to navigate the guide/access catheter 126 near the target treatment site (for example, the guidewire can be placed within one lumen, and then retracted once the treatment site is accessed). Alternatively, core wire 118 which is used with sealing device 110 can function as the guidewire as discussed in previous embodiments where core wire 118 has some degree of freedom of distal movement such that the core wire distal tip 120 can be advanced and the sealing device/system can be advanced over the core wire.

Sealing device 110 is delivered through microcatheter 128, and the sealing device is placed at the distal end of a hypotube pusher as shown in FIGS. 3-4. When guide or access catheter 126 is tracked near the target treatment site (e.g. near the vicinity of the aneurysm), microcatheter 130—which is used to deliver the embolic to the aneurysm, is first pushed out so that it sits within aneurysm 134 (or, alternatively, guide/access catheter 126 is retracted to expose microcatheter 130)—as shown in FIG. 1. Microcatheter 128 is then also pushed out from the delivery catheter (or, alternatively, guide/access catheter 126 is retracted to expose microcatheter 128). Hypotube pusher 122 is then pushed (or microcatheter 128 is retracted) so that sealing device 110 is released from microcatheter 128. The sealing device 110 is placed appropriately under the neck of the aneurysm in order to seal the aneurysm. Sealing device 110 should be placed similar to the configuration shown in FIG. 1, where the cylindrically-shaped medial portion 132c of sealing device 100 seals the neck of aneurysm 134 and where microcatheter 130 is pinned against the sealing device 100. One potential complication of microcatheter 130 being pinned against sealing device 100 is that there may still be a small gap in between the microcatheter 130 and sealing device 100 which results in sealing device 100 not completely sealing the area under the neck of aneurysm 134. This small gap would mainly present toward the proximal portion of the sealing device, since the microcatheter would mainly contact the sealing device on the proximal part of the sealing device (as shown in FIG. 1) and the self-expanding nature of the sealing device would tend to cover some of the open area distal of the interface between microcatheter 130 and sealing device. This small gap could possibly provide an escape path for embolic which could migrate out of the aneurysm and not get caught by sealing device 100. Earlier embodiments discussed one concept where core wire 118 is fixed to distal marker 116 and another concept where core wire distal tip 120 is thicker than marker band 116 and cannot be retracted past marker band 116, and how the core wire can be pulled to radially expand the sealing device. This system can be used to radially expand the sealing device so that no gap is present between the aneurysm and sealing device, which could otherwise allow embolic to seep out of the aneurysm and not get caught by the sealing device. Thus, the user could simply retract wire 118 (see FIG. 1) to expand the sealing device and seal any gap between microcatheter 130 and the area underneath the aneurysm. Since wire 118 can be used to manipulate and control the shape of the expandable sealing device, wire 118 can be thought of as an expandable structure controller/control mechanism. However, note that even if a small gap is present, the blood flow proceeds in a downstream direction (i.e. left-to-right in FIG. 1), so the inclusion of a tight distal mesh/catch structure along distal section 132b, would also help catch the embolic if it leaks. Additionally, microcatheter 130 would, itself, fill much of the proximal gap space.

Figure 9:
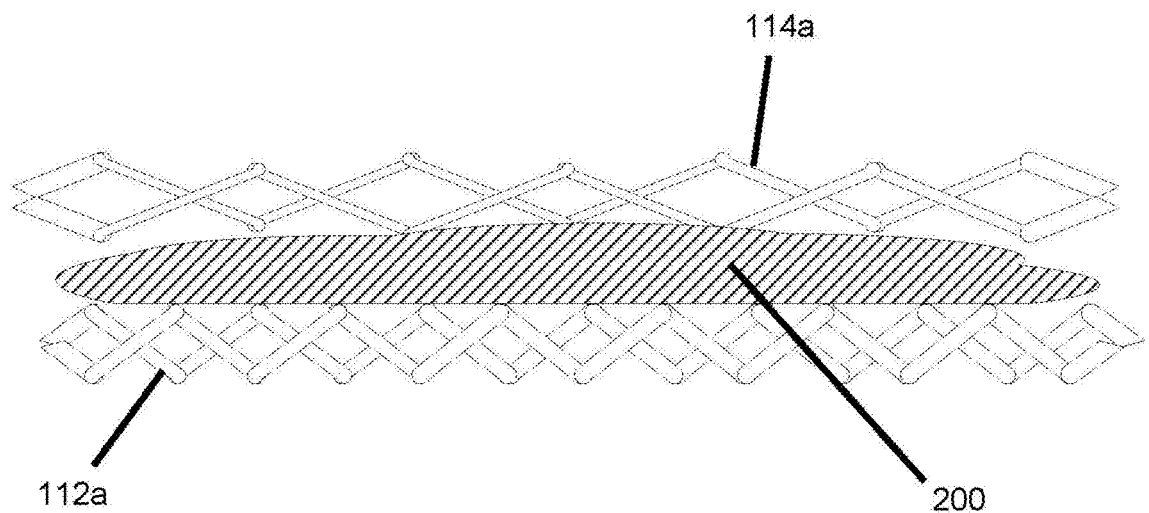
FIG. 9 illustrates a cross-section of a dual-layer sealing device, according to one embodiment, and how liquid embolic would be trapped between the two layers.

Once the liquid embolic starts filling the aneurysm, it may migrate past the neck of the aneurysm prior to solidifying— or portions of the liquid embolic may solidify but still break away from the larger embolic mass. Some embolic may get past the more permeable outer layer (114a, see FIG. 2) of sealing device 110, however the embolic will get caught by the less permeable inner layer of the sealing device. Ideally, there is a small gap in between the inner and outer layers of the sealing device—this small gap provides a catch area for the liquid embolic such that the embolic is caught between the gap defined by the outer 114a and inner 112a layers of sealing device 110. Where attachment means are used between the two layers, as discussed earlier, the number of attachment points or the tightness of the wire wound through the layer will affect the gap size in between the two layers. More attachment points, or a tighter wire winding through the layers would result in a smaller gap; while fewer attachment points or a looser wire winding through the layers would result in a larger gap. These variables can be tweaked to control the size of the gap between the inner and outer layers. The liquid embolic will be captured in between the two layers, forming a thin film of precipitated solidified material. Where a single-layer device (e.g. a single layer stent) is used as an embolic scaffold, a large pore size would allow liquid embolic to freely migrate through the device, which could introduce stroke risk elsewhere in the vasculature. On the other hand, a single-layer device with small pores would result in liquid embolic being trapped outside of the stent, which would make re-sheathing of device very difficult since there would be a thick layer of embolic stuck to the device effectively increasing the overall diameter of the device. In comparison, a multiple-layer sealing device 110 including a tighter mesh inner layer and a looser mesh outer layer—as envisioned in several embodiments of the current invention, would allow for a gap or pocket between the tighter inner layer and looser outer layer to hold the precipitated or solidified liquid embolic—this configuration is shown in FIG. 9 where trapped embolic 200 sits between a loose outer layer 114a and a tight inner layer 112a. The sealing device could still be withdrawn since the inner layer would still be able to collapse upon re-sheathing into a catheter since there is nothing effectively under this inner layer—the act of the inner layer collapsing will help force the outer layer and the embolic pocket to also collapse, allowing the sealing device to be withdrawn from the vasculature after the liquid embolic has sufficiently occluded the aneurysm. In one example, after the embolic delivery procedure, the proximal end of the sealing device is pinned against microcatheter 128 which is used to deliver the sealing device, and the sealing device is retracted into a guide catheter 126 which is used to remove the device from the vasculature.

Another embodiment could utilize an inner balloon and an outer mesh as the sealing device. The microcatheter used to deliver the sealing device would contain an inflation lumen to inflate the balloon once the sealing device is placed. The outer mesh could still be self-expandable, or, alternatively, the balloon inflation would prop the mesh open. Alternative embodiments could utilize multiple mesh layers and an inner balloon, or the embodiment of FIG. 1 with the inclusion of an inflatable inner balloon within the multiple mesh layers. The embolic may get past the outer mesh layer but would be trapped against the balloon.

In one example, the sealing device has an inner and outer layer. The inner layer has a diameter of about 4-5 millimeters, while the outer layer has a diameter of about 4.5-6 millimeters. In one example, the inner layer has a diameter of about 4.2 millimeters and the outer layer has a diameter of about 4.7 millimeters. Note the difference in diameters between the inner and outer layers provides the pocket or gap discussed earlier where any displaced liquid embolic can be trapped or caught. In one example, the inner and outer layers are comprised of a wire mesh where the wires are about 0.0005-0.002 inches in diameter. The inner layer wires can have a different diameter than the outer layer wires, or the wires comprising both the layers can have the same diameter. In one example, the sealing device is configured so that the inner layer pores are about 50-1000 microns, in one example 75-500 microns, in one example about 100-250 microns, in one example about 100-150 microns. A larger pore size would allow blood and DSMO through while also expanding the possibility of liquid embolic getting through, while a smaller pore size would be more likely to block the flow of embolic but an extremely small pore size could block the flow of blood and DMSO.

Various techniques can be used to make the sealing device. For example, the sealing device can be braided over a mandrel where the mandrel includes two tapered ends to create the tapered proximal and distal section shapes shown in FIG. 1. Alternatively, the sealing device is braided over a tubular mandrel and a marker band is placed over the proximal and distal ends to create the tapered shape. Please note, as discussed earlier, the term taper refers to involving a diameter reduction in a particular direction. For the purposes of FIG. 1, the particular shape shown is conical type of taper, though other tapered shapes are possible as will be described.

Figure 8:
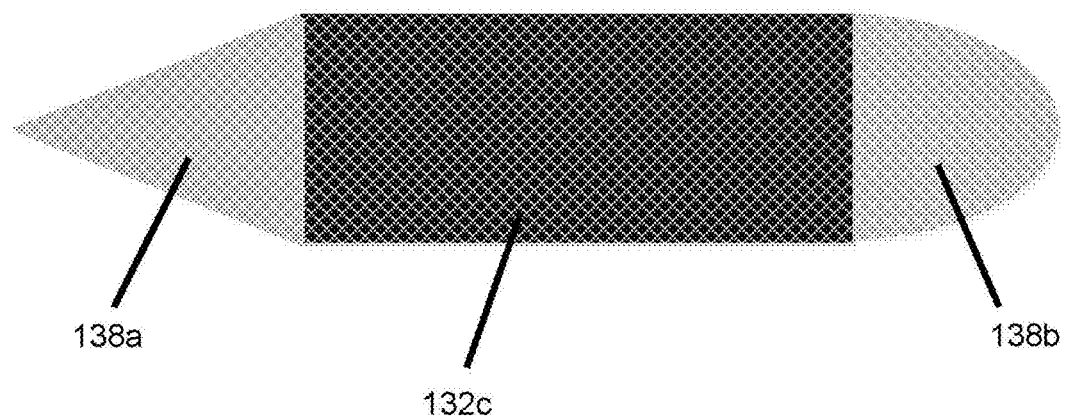
FIG. 8 illustrates a sealing device having a rounded distal section, according to one embodiment.

FIG. 1 show the sealing device with a conically tapered proximal 132a and distal 132b section shape. The sealing device can adopt various shapes, including various proximal and distal section shapes. In one example, proximal section 138a of the sealing device has a conical shape while the distal section 138b of the sealing device can have a rounded shape—as shown in FIG. 8. This shape can be achieved, for example, by utilizing a mandrel with a rounded-end section, where the distal section is braided over the rounded-end section. Alternatively, the proximal end of the sealing device can have a rounded shape while the distal end of the sealing device has a tapered shape. Alternatively, both the proximal and distal ends of the sealing device can have a rounded shape. This shape can be created by utilizing a mandrel with two rounded-end sections to create the sealing device.

The following embodiments shown in FIGS. 10-19 and described below have particular usefulness in treating aneurysms, including bifurcation aneurysms. Bifurcation aneurysms occur at a vessel bifurcation region. Vessel bifurcations are regions of high blood flow and there is a significant amount of pressure exerted on the blood vessel wall in the bifurcation region which can lead to the formation of aneurysms. Bifurcation aneurysms represent the vast majority of aneurysms in the neurovasculature, and if these aneurysms rupture complications such as stroke can result. Bifurcation aneurysms can be difficult to treat since the geometry of the vessel bifurcation region makes placement of stents or other devices difficult since the bifurcation region straddles multiple blood vessels. Often, two stents are placed across each other in a procedure known as y-stenting to cover both branches of the bifurcation. The aneurysm itself can be filled with embolic coils, and the multiple stents retain the embolic coils. Alternatively, two flow diverting stents may be placed together to limit blood flow to the aneurysm. Two-stent procedures are challenging and costly due to the time and expense associated with placing multiple stents. Liquid embolic generally cannot be used to treat bifurcation aneurysms due to the high risk of liquid embolic migration prior to solidification or even after solidification, where the liquid embolic can migrate elsewhere leading to major complications. The following embodiments are geared towards a sealing device that can be placed within the bifurcation aneurysm or against the neck of the bifurcation aneurysm thereby facilitating the use of liquid embolic.

Figure 10:
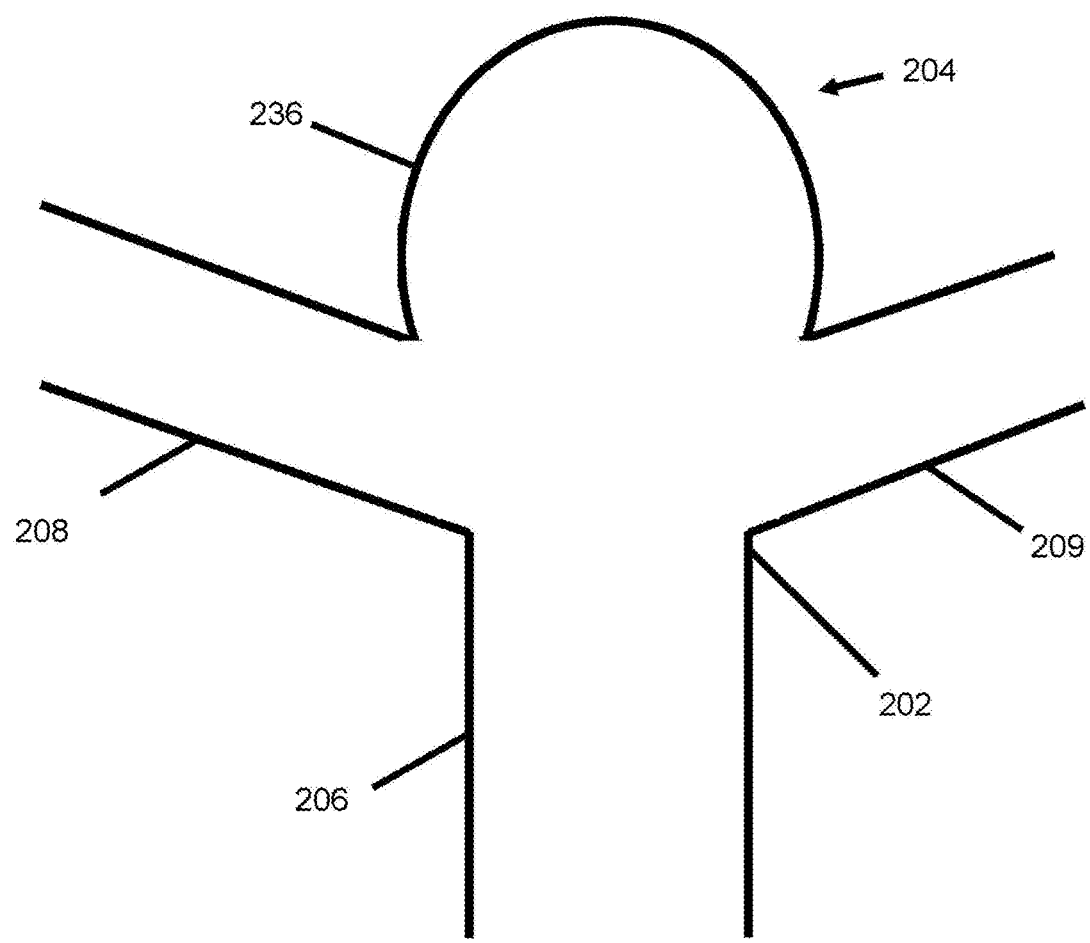
FIG. 10 illustrates a bifurcation aneurysm.

A bifurcation aneurysm 204 is shown in FIG. 10. As shown in the Figure, a bifurcation aneurysm 204 occurs at a vessel bifurcation where a parent vessel 206 branches off into vessels 208, 209.

Figure 11:
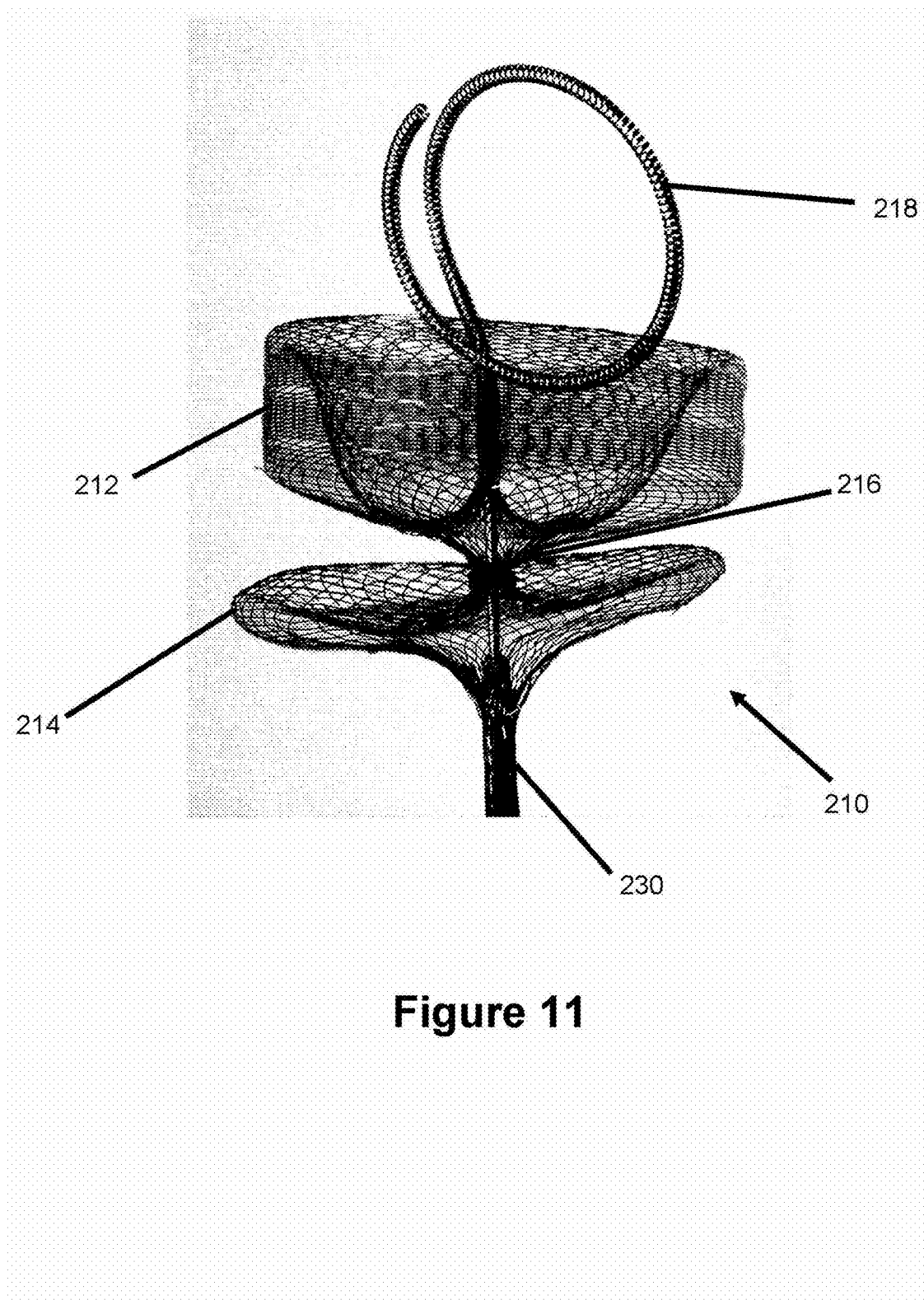
FIG. 11 illustrates an occluder used in a sealing device, according to one embodiment.

FIG. 11 illustrates an occluder 210 used in a sealing device/system, where the sealing system is particularly beneficial in treating bifurcation aneurysms. In one embodiment, occluder 210 is formed of a plurality of metallic braided wires. The wires can be made of nitinol, stainless steel, and/or cobalt-chromium. Nitinol is one particularly preferred material due to its strong shape memory properties. Radiopaque wires (e.g., tantalum, platinum, palladium, and/or gold) can also be incorporated into the braided wire mesh to aid in visibility. Occluder 210 is imparted with a heat set shape, where the wires comprising the occluder 210 are heat set into a particular expanded shape so that the occluder adopts an expanded shape upon delivery from a catheter. The occluder can therefore be thought of as an expandable structure. Occluder 210 includes a distal portion 212 and a proximal portion 214, separated by a band 216. The band is placed over the braid and is used to create a constriction in the occluder to thereby define the distal portion 212 and proximal portion 214. The band can be composed of a metallic (e.g., nitinol or stainless steel) tube or crimp. Alternatively, a radiopaque marker band (e.g. tantalum, platinum, palladium, gold) can be used to aid in visualization. A distal coil 218 is connected to the end of the occluder. Coil 218 preferably has a shape memory coiled shape configured so that when coil 218 contacts the vessel wall, said coil 218 will curl inwards instead of sticking to the wall. In one example, coil 218 is made of nitinol or a radiopaque material such as platinum. When occluder 210 is placed into an aneurysm, coil 218 is the first object to contact the aneurysm dome. Coil 218 contacts the dome of the aneurysm and serves as a base structure which the rest of occluder 210 opens under. The proximal part of occluder 210 is connected to a pusher 230. The pusher tube is tubular in shape and contains an open lumen.

Figure 12:
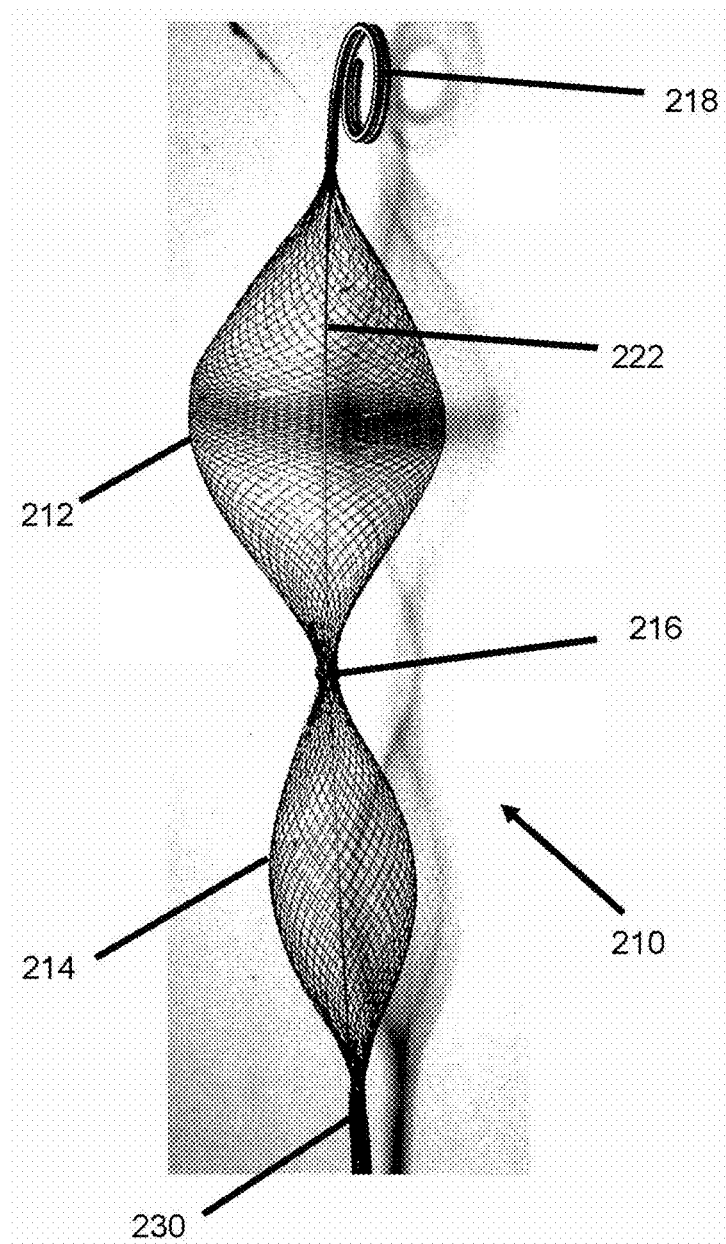
FIG. 12 illustrates the occluder from FIG. 11 in an expanded configuration, according to one embodiment.
Figure 13:
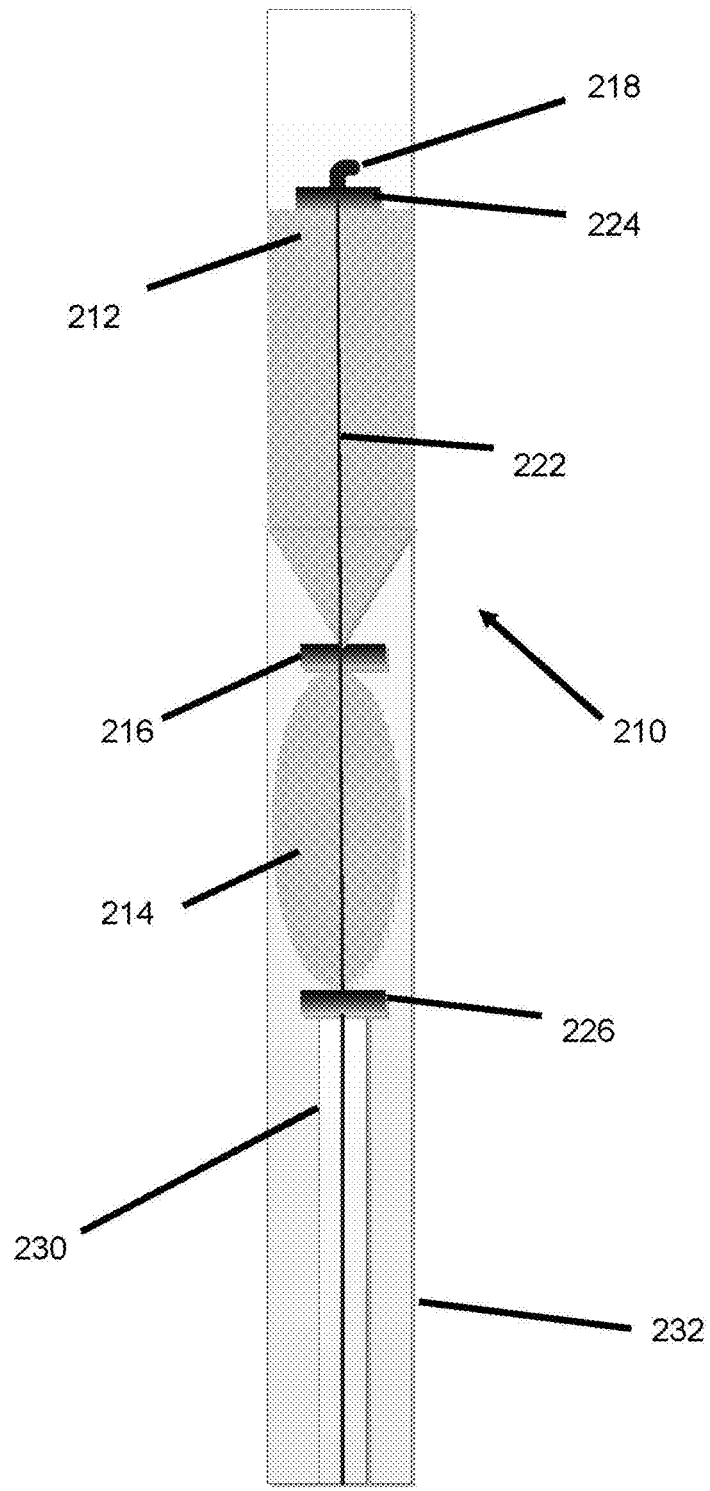
FIG. 13 illustrates a sealing system in a collapsed state during delivery, according to one embodiment.
Figure 14:
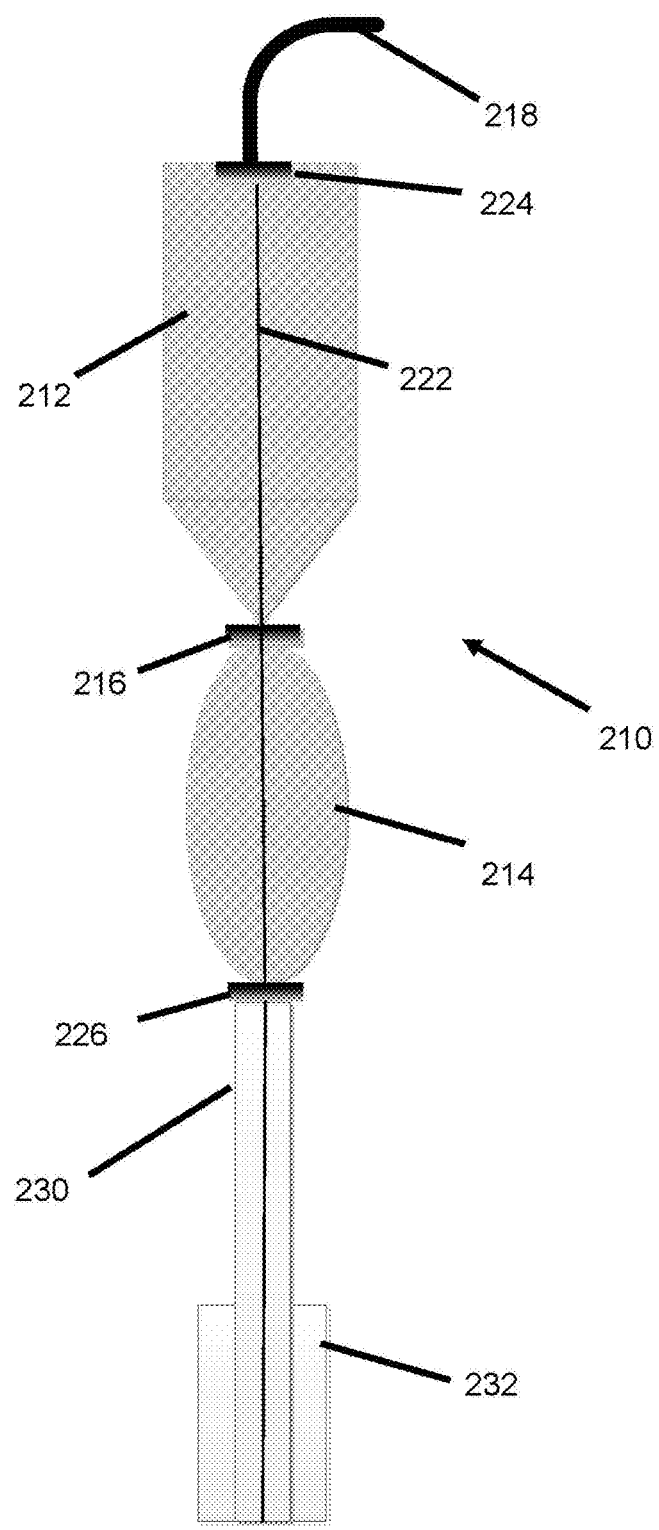
FIG. 14 illustrates a sealing system in a delivered state where an occluder used in the system adopts a stretched configuration, according to one embodiment.
Figure 15:
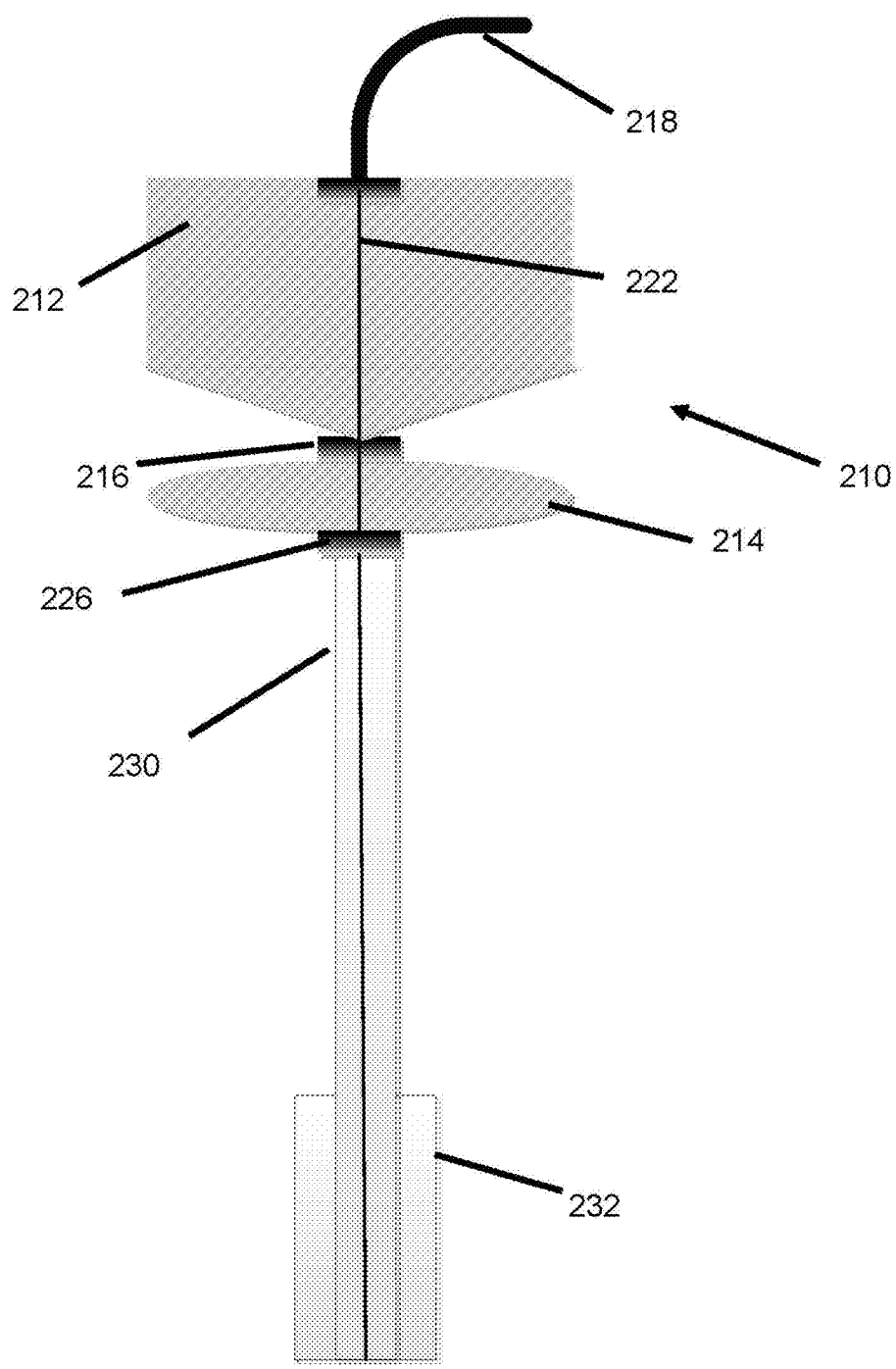
FIG. 15 illustrates a sealing system in a delivered state where an occluder used in the system adopts a radially expanded configuration, according to one embodiment.

A tension wire 222 runs the length of occluder 210 as shown in FIG. 12. The distal end of the tension wire 222 connects to distal coil 218. In one embodiment, the inner surface of coil 218 contains a threaded interface which the distal end of wire 222 can screw into via mechanical rotation. This mechanical connection can be achieved in a couple different ways. For instance, the distal end of tension wire 222 could contain male threads and a portion of the inner lumen of coil 218 could contain female corresponding receivers. Alternatively, coil 218 is placed over a mating structure and the mating structure contains a threaded interface to mate a corresponding interface on the distal end of tension wire 218. Other embodiments could forego distal coil 218 and instead just include an interface structure, such as a cap, that the tension wire can mechanically connect to (e.g. via the male/female threaded rotation concepts discussed above). Tension wire 222 spans the length of pusher 230. Pusher 230 is a tube and contains an open lumen spanning the length of the pusher which accommodates tension wire 222, as shown in FIGS. 13-15. Tension wire 222 and pusher 230 are separately controlled and manipulated by a user from the proximal end of the system; the proximal end of tension wire 222 sits proximally beyond the proximal end of pusher 230 so that the tension wire and pusher are independently pushed/pulled. Pushing or pulling the pusher will push or pull the entire system, while pushing or pulling the tension wire will manipulate the shape of occluder 210 in a manner which will now be described. The distal part of the tension wire 222 is connected to coil 218, but this is the only part of the tension wire 222 connected to anything. Therefore pushing tension wire 222 will exert force on coil 218 thereby pushing the coil and the attached occluder 210 thereby elongating occluder 210 so that it takes on the shape shown in FIG. 12. Pulling tension wire 222 will exert a retracting force on coil 219 thereby pulling the coil and the attached occluder 210 back so that the occluder 210 takes on the compressed shape shown in FIG. 11. Since tension wire 222 can be used to manipulate and control the shape of the expandable occluder 210, wire 222 can be thought of as an expandable structure controller/control mechanism. Occluder 210 can include folding layers where the layers fold into each other as the occluder 210 collapses when the tension wire is retracted or pulled. The folding layers would allow a significant amount of material to be used on the occluder, but where the occluder adopts a smaller profile when compressed allowing for a substantial difference between the compressed and elongated shape of the occluder.

FIG. 13 shows the sealing system, including occluder 210, during delivery through a larger delivery catheter 232. In one example, delivery catheter 232 is a 6 or 7 French guide or access catheter and pusher 230 is 2-3 French size—this would represent a relatively larger system since embolic devices are typically delivered through 2 or 3 French size microcatheters. In another example, delivery catheter 232 is a 2 or 3 French size microcatheter, and the pusher is 1-2 French size to be accommodated within the microcatheter. Occluder 210 is sheathed within delivery catheter 232 and is navigated or pushed through delivery catheter 232 to the treatment site. Occluder 210 takes on an elongated configuration when placed within the delivery catheter due to the restraining force provided by delivery catheter 232, as illustrated in FIG. 13. The user pushes pusher 230 to navigate the sealing system through delivery catheter 232. Tension wire 222 can also be separately pushed while pusher 230 is pushed during delivery to keep tension on the occluder and ease delivery by minimizing the portion of occluder 210 contacting the delivery catheter 232 inner wall during delivery, thereby minimizing friction. There is a detachable connection 226 between pusher 230 and occluder 210 which can be detached to sever the occluder from the pusher, which will be described in more detail later. Element 224 represents the attachment mechanism connecting tension wire 222 to distal coil 218.

Figure 16:
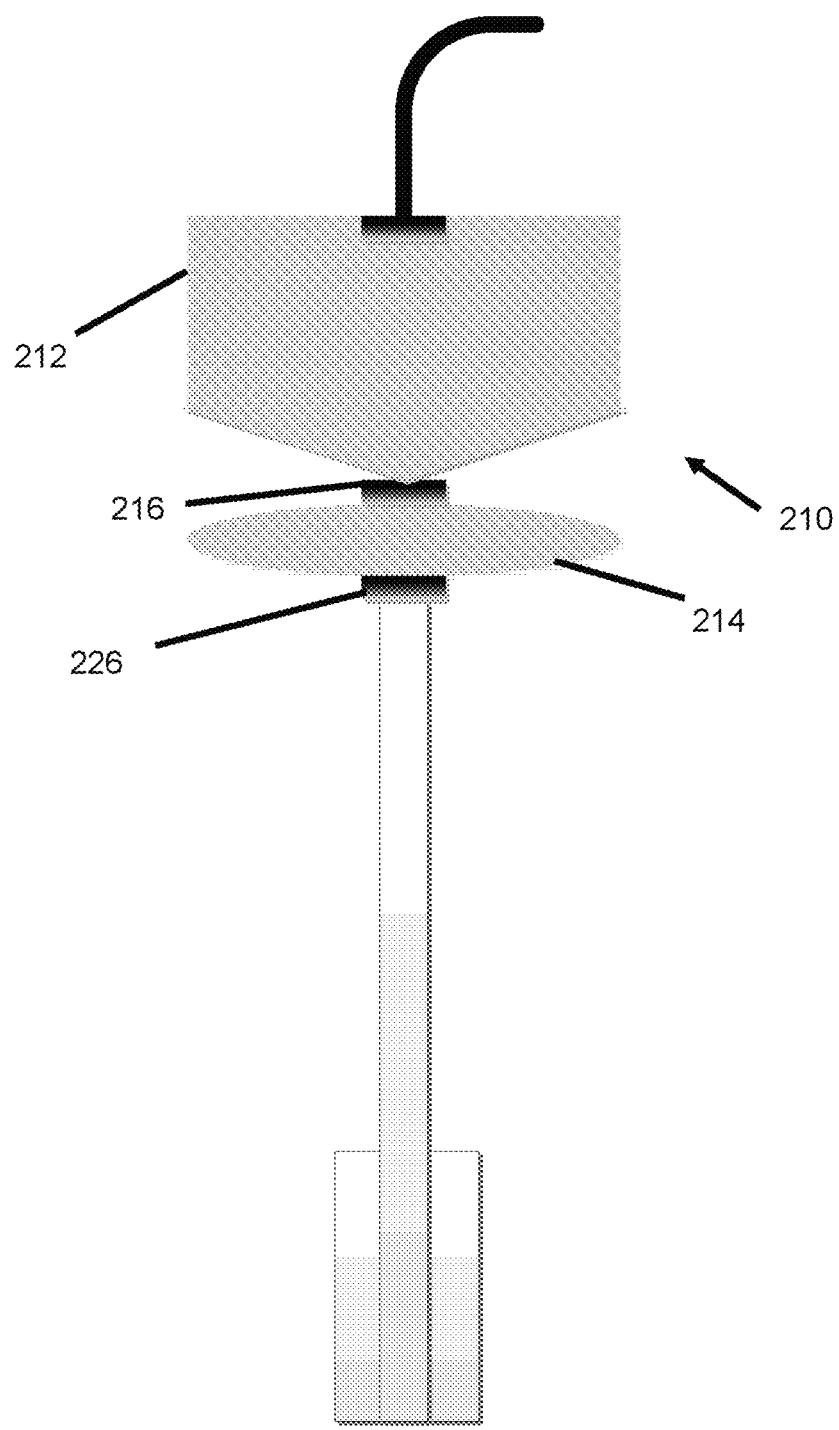
FIG. 16 illustrates the sealing system of FIG. 15 where the tension wire is withdrawn, according to one embodiment.

FIGS. 14-15 show the occluder 210 after being pushed out of delivery catheter 232. Occluder 210 will adopt an expanded configuration after being released from delivery catheter 232 due to the enlarged heat set shape imparted into the occluder. In FIG. 14, tension wire 222 is pulled to collapse the shape of occluder 210, thereby enabling the occluder to adopt a longitudinally contracted, radially expanded shape. Occluder 210 would be delivered to the target treatment site, and tension wire 222 is then pulled to collapse the shape of occluder 210 in order to fit the shape of the treatment area. When the shape of occluder 222 is appropriately configured for the treatment area, tension wire 222 is withdrawn—in the embodiment where the tension wire is a mechanically screwing connection, the tension wire can simply be unscrewed and then pulled out from pusher tube 230—as shown in FIG. 16. The tension wire would preferably be pushed/pulled so that the proximal portion 224 of occluder 210 is as wide as possible to conform to the bottom portion of the aneurysm 236 while still fitting within said aneurysm. Since the occluder proximal portion 224 would generally abut or be near the aneurysm neck, it should be as wide as possible to prevent embolic migration past this layer.

Figure 17:
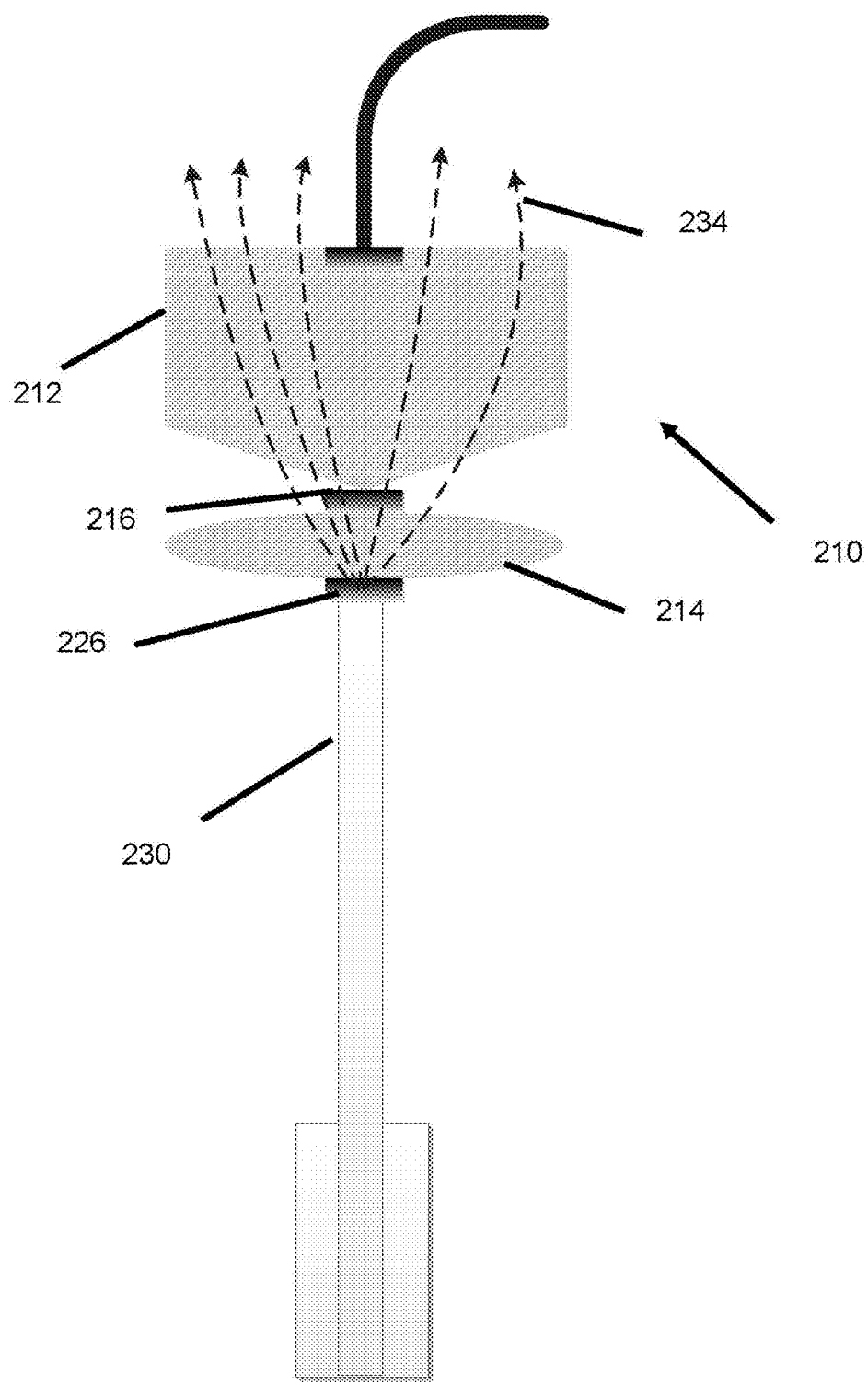
FIG. 17 illustrates a sealing system after delivery to a target site, according to one embodiment, where a pusher tube is used to deliver embolic.

Once the wire is withdrawn, pusher tube 230 can be used to deliver additional embolic agents, including liquid embolic and/or other agents including embolic coils or meshes. In FIG. 17, pusher tube 230 is used to deliver liquid embolic 234. It is beneficial to remove tension wire 222 from pusher 230 prior to embolic delivery in order to maximize the lumen space for embolic delivery, however, if tension wire 222 is sufficiently narrow then it might not be necessary to remove tension wire 222 prior to embolic delivery. The liquid embolic is delivered into the target treatment site. The liquid embolic, delivered in a liquid form, will easily pass through the pores of occluder 210. The pores of occluder 210 will also allow the DMSO to diffuse out of the occluder, as the DMSO diffuses from the liquid embolic after delivery. The porous mesh occluder 210 will also allow blood to flow through, as blood is displaced due to delivery of the liquid embolic. As the liquid embolic is exposed to blood, the embolic starts to precipitate. As the embolic precipitates, it gets more viscous and can no longer pass through the pores of occluder 210; the embolic then solidified and occludes the target space. The embolic, therefore, is contained within the aneurysm/treatment site. In one embodiment, occluder 210 includes a polymer coating to further aid in embolic retention; the polymer coating would increase the thickness of occluder 210 and reduce the pore size, therefore offering some additional advantages in embolic retention. The polymer coating can be applied in selective places along the occluder 210, so that there are still porous openings present to allow diffusion of blood and DMSO through occluder 210. In one embodiment, the mesh of proximal section 214 is less porous than the mesh of distal section 212; this can be achieved by utilizing smaller pores on proximal section 214, which would ensure that liquid embolic is less likely to pass through proximal section 214 and permeate beyond the aneurysm. In one embodiment, the polymer coating could be utilized solely along the proximal section mesh 214 in order to decrease the porosity in this region to help prevent embolic passage past this region. In one example, the mesh pore sizes are configured so that they are about 50-1000 microns, in one example about 75-500, in one example about 100-250 microns, in one example about 100-150 microns.

After the liquid embolic 234 is delivered and precipitates, pusher tube 230 is withdrawn. There is a detachment junction 226 between pusher 230 and occluder 210 which can be severed to separate said pusher from said occluder. Various types of detachment systems can be used, for instance mechanical, thermal, or electrolytic systems. U.S. Pat. No. 8,182,506, US20060200192, US20100268204, US20110301686, US20150289879, US20151073772, US20150173773 all of which are hereby incorporated by reference in their entirety, disclose various detachment systems that could be used with the present concept. Detachment junction 226 includes a severable linkage, for example a detachable tether or degradable substance which degrades thermally, mechanically, or electrolytically to effect detachment of the occluder. In one example, the user would activate a user interface (i.e. button) to degrade a portion of the detachment junction to effect detachment between the pusher 230 and occluder 210.

Figure 18:
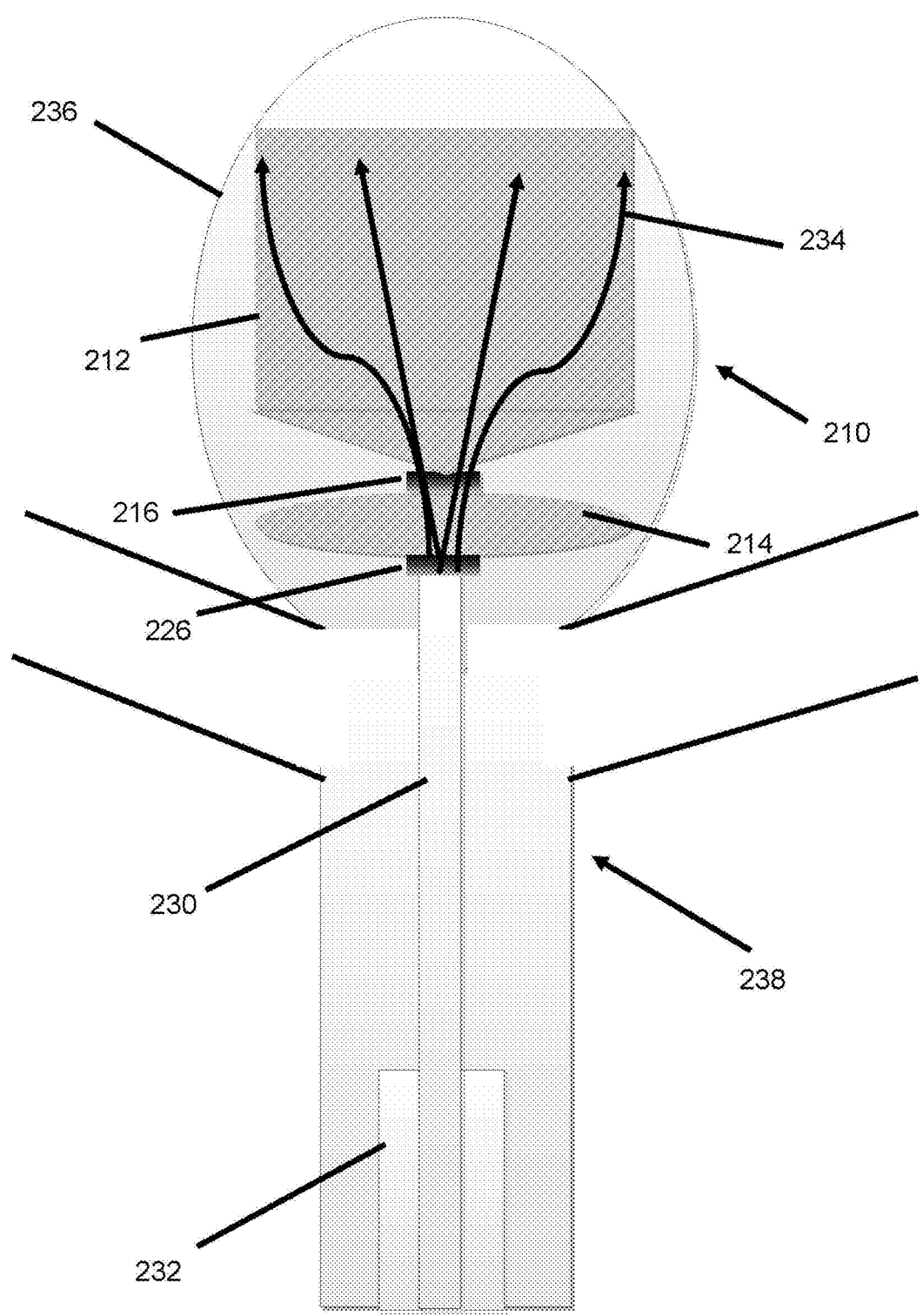
FIG. 18 illustrates a sealing system used in a bifurcation aneurysm, according to one embodiment, where liquid embolic is delivered into the bifurcation aneurysm.
Figure 19:
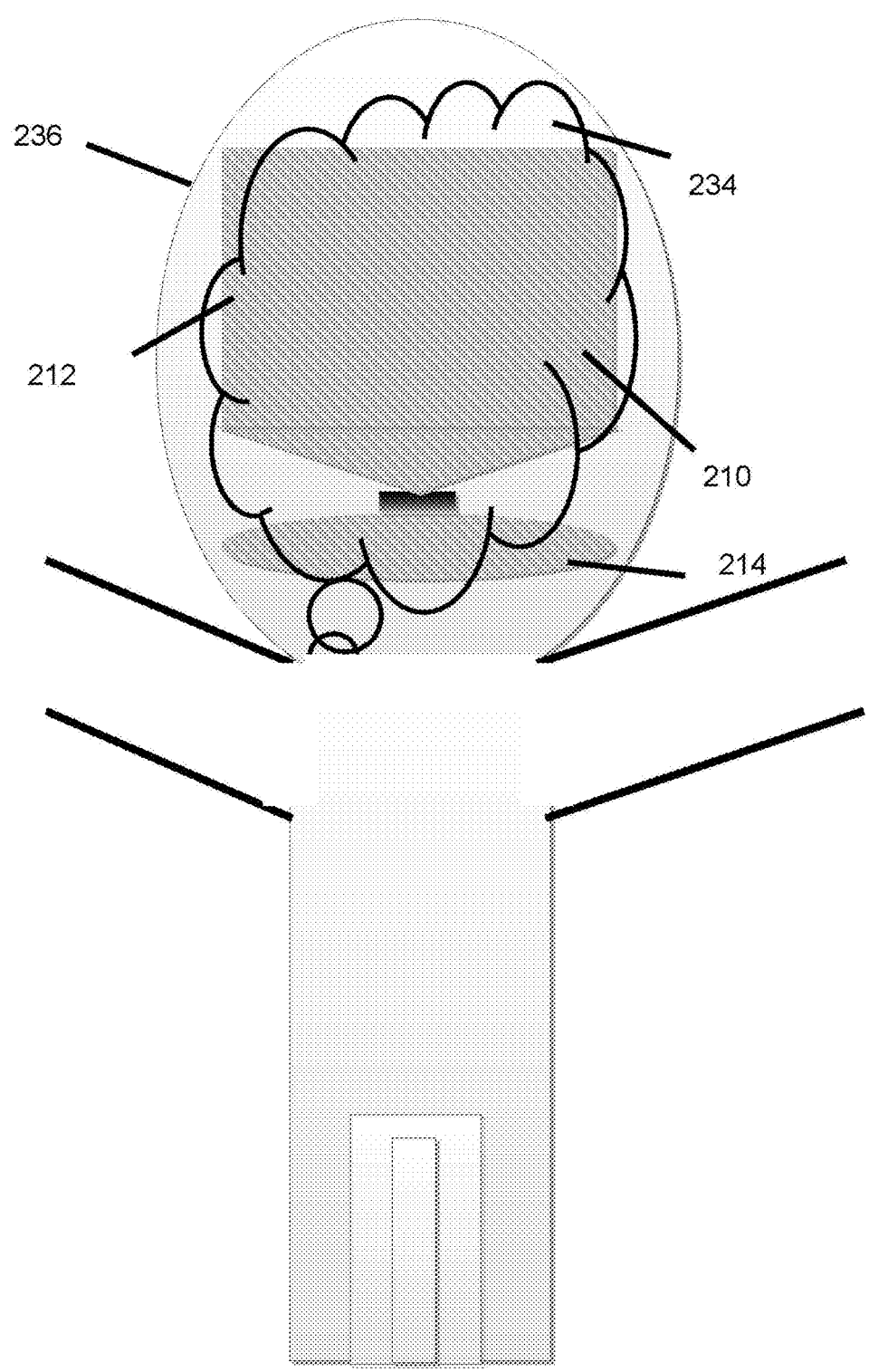
FIG. 19 illustrates a sealing system used in an aneurysm, according to one embodiment, where delivered liquid embolic has solidified to create an occlusive mass along with an occluder.

FIGS. 18-19 show the treatment procedure within a bifurcation aneurysm 236. The sealing system is delivered through blood vessel 238 into bifurcation aneurysm 236. Due to the manipulatable shape of occluder 210, the occluder sits physically within the vessel and prevents subsequently delivered liquid embolic from seeping out.

In one embodiment, the distal portion 212 of occluder 210 sits within the aneurysm and proximal portion 214 of occluder 210 sits outside of the aneurysm, proximal section 214 would in essence act like a neck seal ensuring embolic does not escape the neck of the aneurysm. In another embodiment, occluder 210 sits completely outside the aneurysm and the while occluder acts like a neck seal or catch sitting flush with the neck of the aneurysm and preventing embolic from migrating.

Arterio-venous malformations (AVM's) are abnormal connections which form between the arteries and veins. Arteries supply oxygen-rich blood from the heart to various areas of the body, while veins return oxygen-poor blood to the heart. Capillaries normally connect arteries and veins, allowing the exchange of oxygen, water, and nutrients with the brain and brain tissue. AVM's often take form as a tangled mass of connections, which bypass the normal capillary system entirely, bypassing normal brain tissue and interfering with natural blood flow. The vascular abnormality of malformed blood vessels is typically referred to as the nidus. AVM's can form in a number of locations but often form in the brain, and there is a risk of hemorrhage which can result in stroke. AVM's, like capillaries, contain an arterial side (connecting to the arteries) and a venous side (connecting to the veins).

Figure 20A:
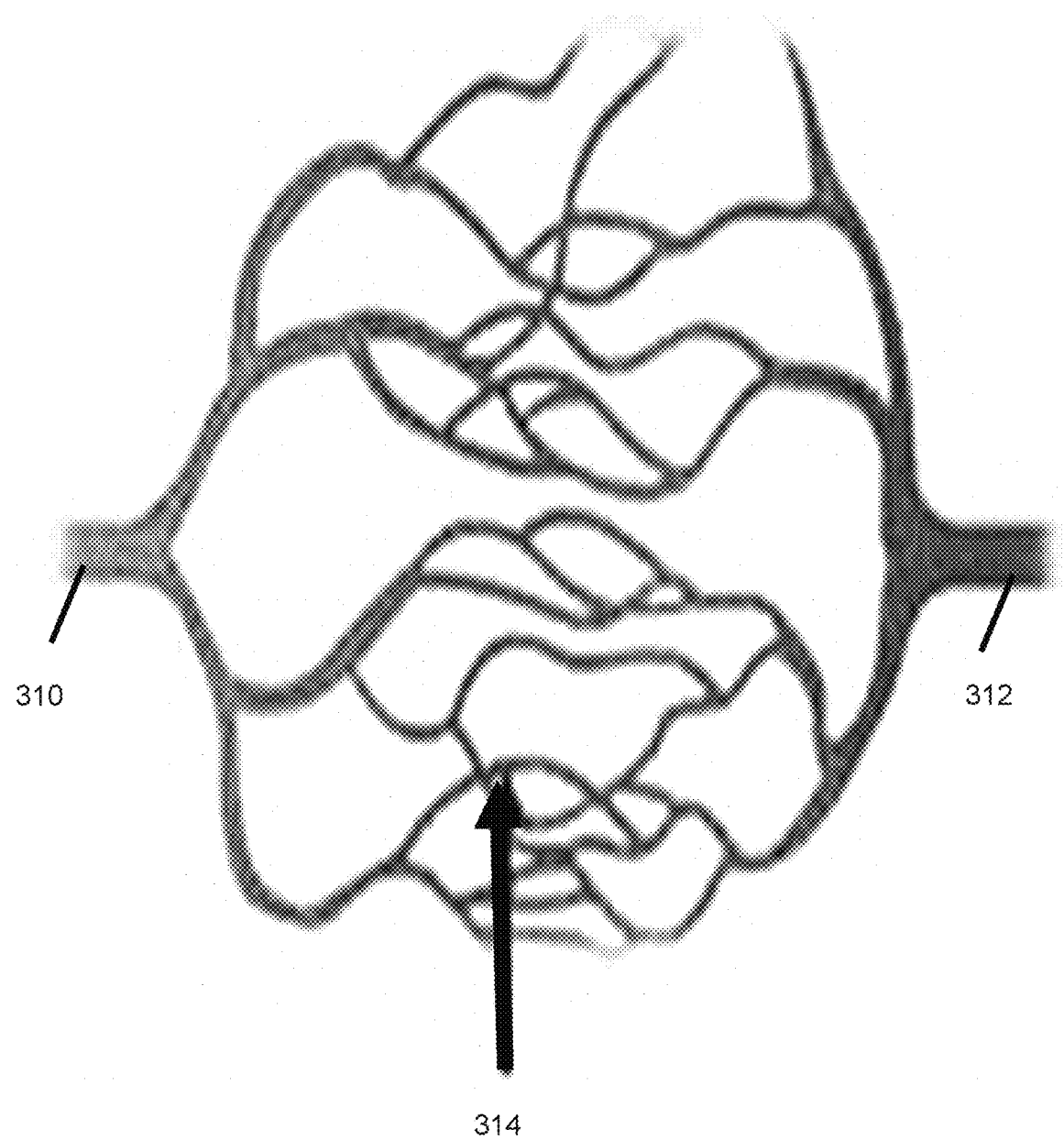
FIG. 20a illustrates a normal arterial-capillary-venous intersection.
Figure 20B:
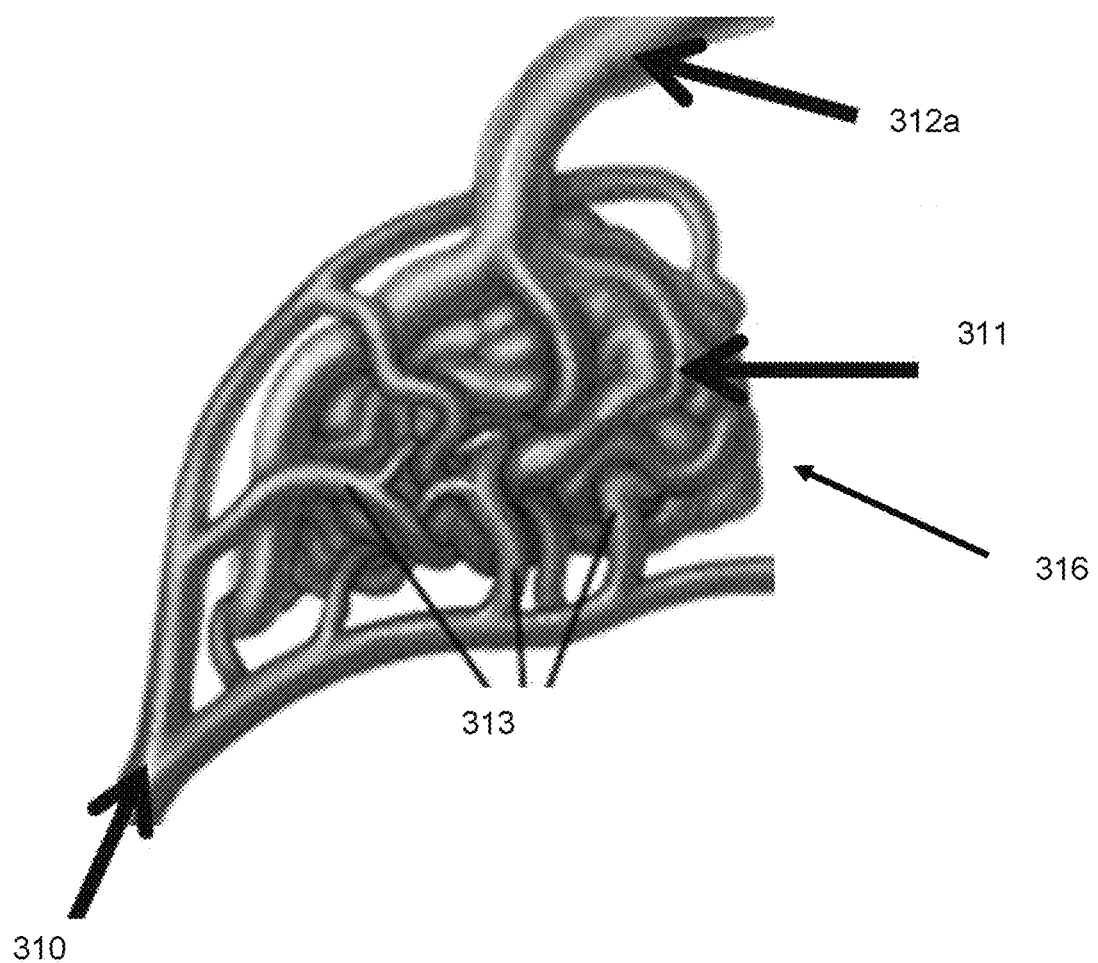
FIG. 20b illustrates an arteriovenous malformation (AVM), including the nidus, feeder vessels, and draining vein.
Figure 21:
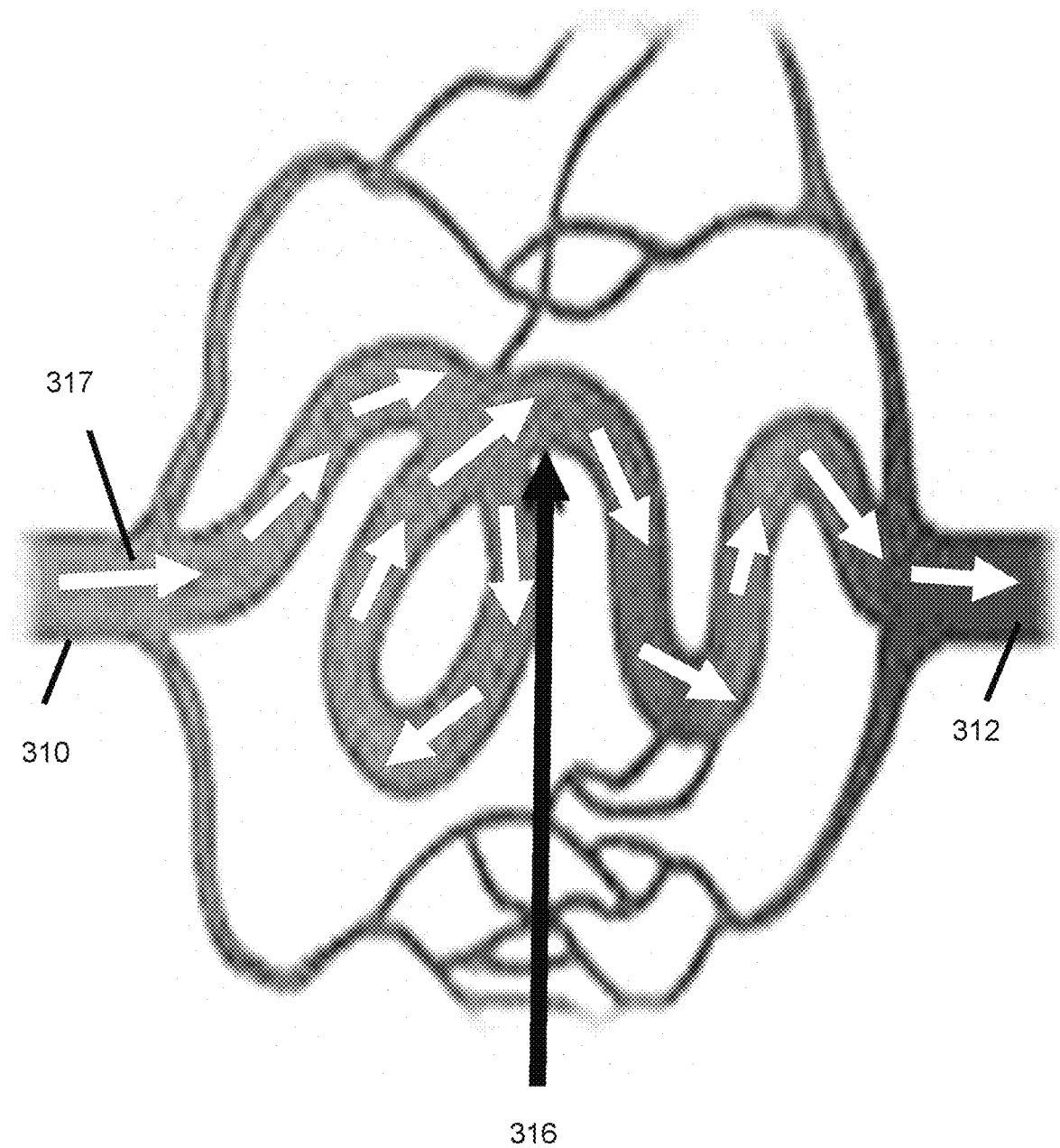
FIG. 21 illustrates an arteriovenous malformation (AVM), along an arterial-venous intersection.

FIG. 20a shows a normal arterial-capillary-venous intersection, comprising an arterial-side 310, venous-side 312, and capillaries 314 which connect the arteries and veins. FIG. 20b shows an AVM 316, which is an abnormal connection between arteries and veins bypassing the normal capillary structure. The AVM includes nidus 311, feeder vessels 313, and draining vein 312. Nidus 311 is an abnormal tangle of blood vessels which draws blood flow away from the capillaries, feeder vessels 313 feed blood into the nidus and away from the capillaries, while an enlarged draining vein 312 provides a flow path out of the nidus into the normal venous system—note since the AVM bypasses the normal capillary system, a draining vein is generally needed to drain the blood into the actual venous system to provide outflow for blood. AVM's are unnatural connecting structures and interfere with the normal circulation pattern, drawing blood away from the capillaries. Over time, AVM's can hemorrhage which can lead to various complications. Please note, AVM's can take on extremely tortuous shapes with many different connections, for the ease of illustration with the proposed treatment concept, a relatively "simple" AVM shape is shown in FIGS. 21-24.

Please note, blood in the artery would flow in the direction of the AVM/capillary, while blood in the veins would carry blood away from the AVM/capillaries. So, in FIGS. 20-22, blood would generally flow left to right—from the artery to the vein, as indicated by the arrows 317 in FIGS. 21-24.

AVM's can occur in various locations throughout the body, including in the neurovasculature and the brain. Neurovascular AVM's are particularly problematic and can rupture leading to stroke. Some treatment procedures to treat AVM's involve occluding AVM's with liquid embolic so that blood flow bypasses the AVM and normal circulation is restored. In the typical procedure, a microcatheter connected to a liquid embolic is tracked through the arterial vasculature to the arterial side of an AVM, near the nidus. Liquid embolic is then injected through the microcatheter and into the AVM. The liquid embolic hardens or solidifies, blocking off passage of blood through the AVM and restoring flow to the capillaries and normal circulation.

One issue with the traditional method of liquid embolic delivery is that too much liquid embolic may be delivered and some embolic may migrate out of the AVM, or the embolic may migrate before hardening and migrate through the AVM and into the venous system. In situations where the AVM is located in the neurovasculature and liquid embolic is used to treat the AVM, the neurovasculature venous path drains into the pulmonary system—so embolic in the venous system can potentially end up in the lungs, leading to major complications. Embolic solidifying in the venous flow path can also close the natural outflow of blood, which can cause the AVM to rupture.

Figure 22:
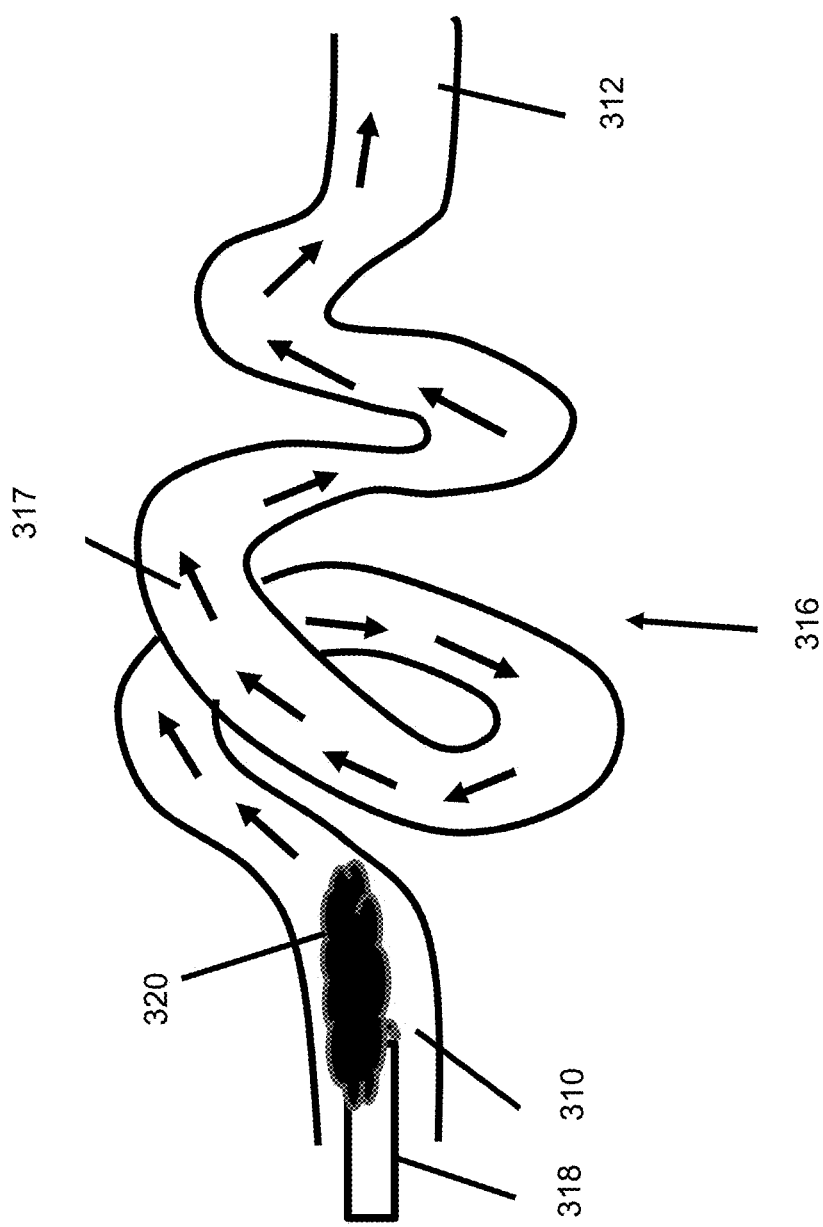
FIG. 22 illustrates a typical delivery procedure to occlude an AVM with liquid embolic.

The typical liquid embolic delivery procedure involves gaining access through the arterial vasculature through the femoral artery. The general procedure involves using a guidewire which is navigated up through the femoral artery to the vicinity of the treatment site. A guide or access catheter is tracked over the guidewire to access the part of the vasculature containing the AVM. A smaller microcatheter is then tracked through the guide or access catheter to the actual treatment site—for instance, through one of the feeder vessels and into the AVM. A proximal part of the microcatheter (the microcatheter hub) is connected to a liquid-embolic containing syringe, and the liquid embolic is delivered from the syringe, through the microcatheter, and then into the AVM. FIG. 22 shows this traditional method of delivery, where microcatheter 318 is passed through the arterial side 310 of AVM 316. Microcatheter 318 is placed in/near the nidus of the AVM and liquid embolic 320 is delivered into the AVM. Since liquid embolic is delivered from the arterial side of the AVM, the embolic is delivered in the direction of blood flow (see arrows 317 in FIG. 22), making it more likely that the embolic will be pushed with the direction of blood flow out of the AVM and into the venous system.

The more specific typical delivery procedure would involve using an introducer to gain access to the femoral artery. A guidewire is then used to navigate to the treatment site. This would involve traversing the femoral artery, external iliac artery, descending aorta, aortic arch, and internal carotid arteries where the guide or access catheter is tracked over the guidewire. Beyond the carotid arteries are the neurovascular arteries which are typically fairly small so generally a microcatheter would then be tracked through the guide or access catheter and used to access the smaller neurovascular arteries including the particular region where the AVM is. The microcatheter is navigated to the AVM, preferably to the feeder vessel leading to the nidus of the AVM. Liquid embolic is then delivered from a syringe mated to the microcatheter hub into the AVM to embolize the AVM. Alternatively, access can be achieved by the introducer gaining access from the carotid artery then navigating to the AVM from the carotid artery.

Figure 23:
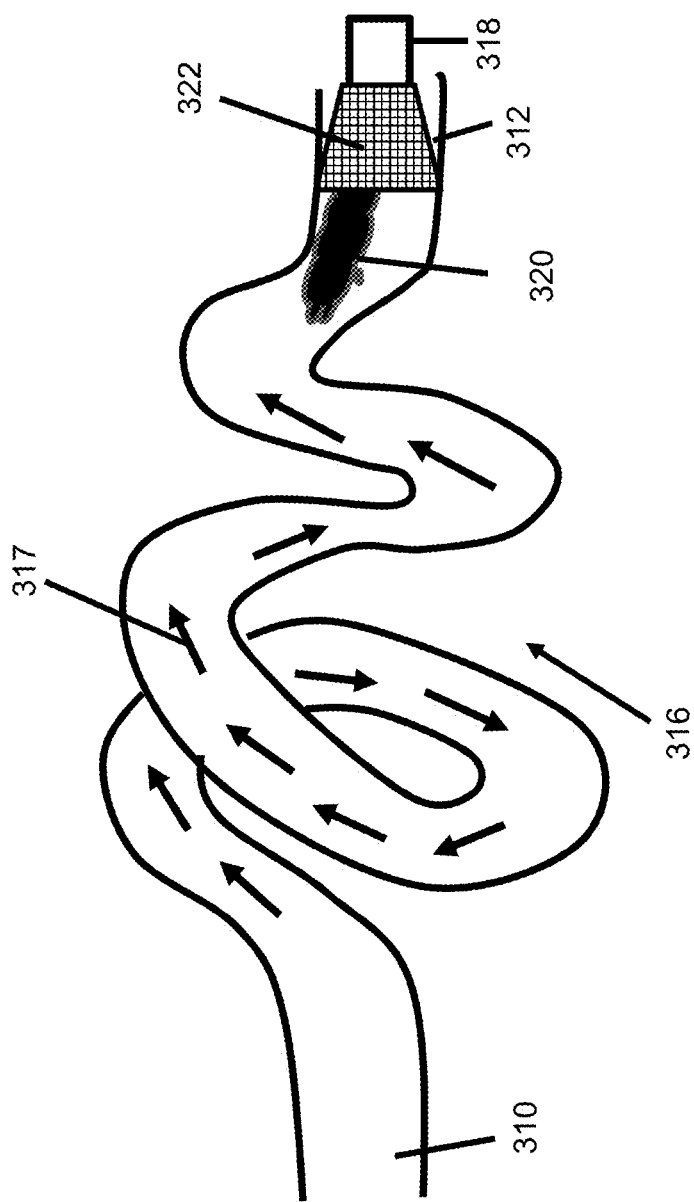
FIG. 23 illustrates a liquid embolic delivery procedure to occlude an AVM, according to one embodiment, utilizing a microcatheter with a catch/shield which is used to deliver liquid embolic from the venous side of an AVM.

One way to deal with the issue of embolic migration which is contemplated in the present invention involves delivering the embolic from the venous side 312 of AVM 316 as shown in FIG. 23—instead of from the arterial side 310 as per the typical embolic delivery procedure shown in FIG. 22. The femoral vein or jugular vein is used to access the venous vasculature, and a guidewire and guide catheter are tracked through the venous system to a location near the AVM 316. A microcatheter 318 is tracked through the guide or access catheter to the venous side 312 of AVM 316, for instance through the draining vein of the AVM. Liquid embolic 320 is then delivered from a syringe coupled to the hub of microcatheter 318 through the microcatheter lumen and into the AVM 316. Since the delivery is from the venous side 312 of AVM 316, the microcatheter placement and liquid embolic delivery will be against the flow of blood, where the arterial to venous flow of blood is indicated by arrows 317 in FIG. 23. Since liquid embolic 320 is delivered against the flow of blood and since liquid embolic is more viscous than blood, liquid embolic will not permeate past the AVM into the arterial system. The relatively high viscosity of liquid embolic compared to blood makes embolic backflow or reflux unlikely even in circumstances where the liquid embolic is delivered against the natural blood flow, however, the microcatheter includes a catch or shield structure 322 to catch any embolic that happens to reflux.

In one example, an introducer is used to gain access through the femoral vein, and a guidewire is used to track through the venous system. A guide or access catheter is then navigated through venous system over the guidewire to the location of the AVM, this would include navigating through the femoral vein, iliac vein, vena cava, through the jugular vein. A microcatheter would then be used to locate the actual region of the AVM, where the microcatheter could be tracked over the guidewire. The microcatheter is preferably placed near/in the drainage vein of the AVM where liquid embolic is then delivered from the microcatheter into the AVM. In another example, access is gained directly through the jugular vein (instead of the femoral vein) and the microcatheter is then navigated through the treatment site.

Placing a microcatheter in the venous system would require delivery against the flow of blood. The microcatheter could be configured for delivery through the venous system by having augmented pushing strength for venous delivery. Microcatheters typically use structural strengthening features such as coils, braids, and particular polymers to augment either pushing strength or flexibility, so these parameters could be tailored for venous delivery.

Figure 24:
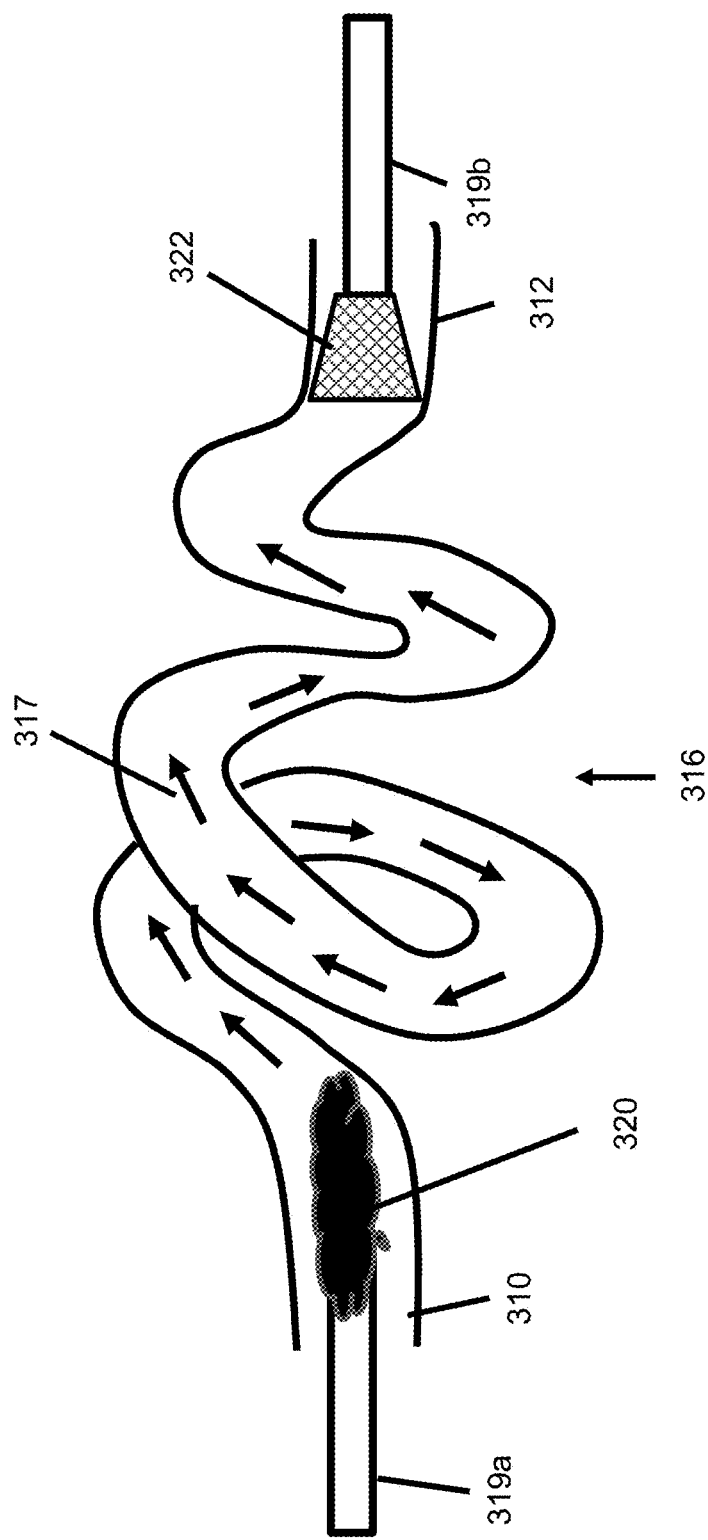
FIG. 24 illustrates a liquid embolic delivery procedure used to occlude an AVM, according to one embodiment, utilizing a first microcatheter to deliver liquid embolic from the arterial side of an AVM and a second microcatheter with a catch/shield used to catch embolic on a venous side of an AVM.

Another way of dealing with the issue of embolic migration, contemplated in the present invention, involves delivering embolic from the arterial side 310 of the AVM but placing a catch or shield on the venous side of the AVM to catch any migrating embolic—as shown in FIG. 24. This would involve the use of two microcatheters—a first microcatheter 319a used to deliver liquid embolic is delivered to the arterial side 310 of AVM 316 while a second microcatheter 319b with catch 322 is delivered to the venous side 312 of AVM 316. The liquid embolic is injected through microcatheter 319a placed on the arterial side of the AVM, in the direction of blood flow as indicated by arrows 317—this is similar to the traditional delivery procedure. However, unlike in the typical delivery procedure, microcatheter 319b and catch/shield 322 are placed on the venous side of the AVM and will catch any migrating embolic. In one example, vascular access is gained through the femoral artery and the microcatheter 319a is tracked through a guide or access catheter to the arterial side 310 of AVM 316. Vascular access for microcatheter 319b is gained through the femoral or jugular vein where microcatheter 319b is tracked through a guide or access catheter to the venous side 312 of AVM 316.

Another embodiment which would deal with the issue of embolic migration is conceptually similar to the embodiment of FIG. 24, except both microcatheters 319a and 319b would deliver liquid embolic. Both microcatheters 319a and 319b are connected to liquid-embolic containing syringes, where said syringes are mated to the microcatheter hubs. Liquid embolic would be delivered through both microcatheters and into the AVM 316, from opposite sides of AVM 316. In this embodiment, rather than relying on embolic occlusion from one side of the AVM, the AVM would be occluded from both sides which would offer some advantages to ensure successful occlusion of the AVM. The presence of the catch or shield structure 322 on microcatheter 319b would ensure any embolic that might migrate from AVM 316 into the venous system would be trapped by shield 322.

FIG. 23 shows a microcatheter 318 with a catch or shield 322. The microcatheter has an inner lumen for injection/delivery of embolic material. The microcatheter inner lumen can accommodate a guidewire that permits navigation and guiding of the microcatheter such that the microcatheter can be tracked over the guidewire and through the guide or access catheter. In one embodiment, the catch or shield 322 is comprised of a mesh of metallic wires. The mesh could comprise nitinol wires, braided together to form the shield—nitinol is a material with particularly good shape memory retention properties. Alternatively, radiopaque (i.e. gold, platinum, tantalum, palladium) wires could be incorporated along with the nitinol wires in the mesh in order to aid in visualization. Shield 322 could also comprise various materials such as cobalt-chromium, stainless steel, polymers. Shield 322 is preferably comprised of biocompatible materials since the shield will be placed within the vasculature. The mesh preferably has smaller pores; the pore size should be large enough to allow relatively unimpeded flow of blood and DMSO, but small enough to prevent the passage of the heavier and more viscous embolic material—especially as the liquid embolic starts to gets thicker and solidify after exposure to blood. In some examples, the pore size could be about 50-1000 microns, about 75-500 microns, about 100-250 microns, or about 100-150 microns. The shield can be thought of as a tight-knit mesh/braid basket meant to catch embolic material. The shield will trap the liquid embolic agent as it is precipitating, while permitting flowing blood to still pass through the shield until the AVM is fully occluded—once the AVM is fully occluded there will be minimal or no blood flow through the AVM due to the occluding effect of the solidified embolic. In one example, the user would inject the liquid embolic until the embolic fills past the AVM nidus on the arterial side to penetrate the arterial feeder vessels to shut off the blood flow into the AVM, eliminating any blood flow path into the AVM. Once the AVM is fully occluded, the risk of an AVM rupture is low since there is no longer any blood flow into the AVM. Additionally, once the liquid embolic has precipitated or solidified, the embolic should stay in place since it will be a homogenous solidified mass occluding the AVM. Different embodiments could also utilize a variable pore size along the length of shield 322 where, for instance, a distal portion of shield 322 (the part closer to AVM 316) can utilize a higher porosity than a more proximal portion of shield 322—due to the conical shape of shield 322, this would mean the outer distal region of the shield would be more permeable than the inner proximal region of the shield. In practice, this should funnel blood and DMSO through the outer, more-porous part of the shield while the inner, less-porous part of the shield would offer increased resistance to blood and DMSO flow, such a configuration could maximize the chances of catching embolic since the catch as a whole would offer more resistance to flow since only a particular region of the shield would allow relatively unimpeded flow of blood and DMSO.

Figure 25:
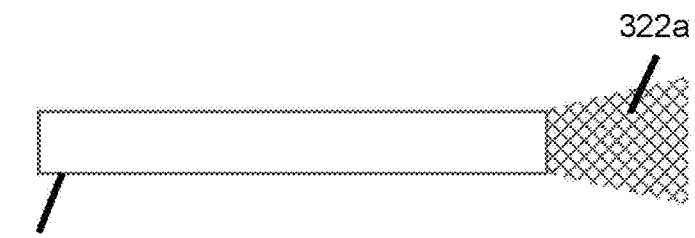
FIG. 25 illustrates a catheter with a conically-shaped catch, according to one embodiment.
Figure 26:
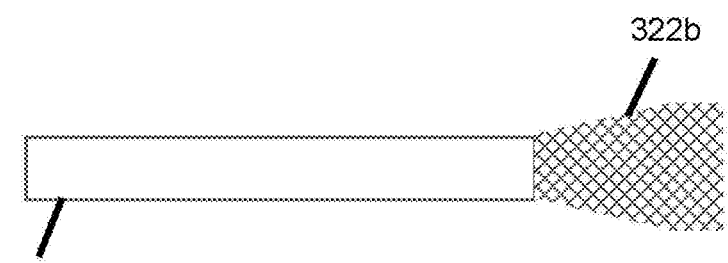
FIG. 26 illustrates a catheter with an elongated-shaped catch, according to one embodiment.
Figure 27:
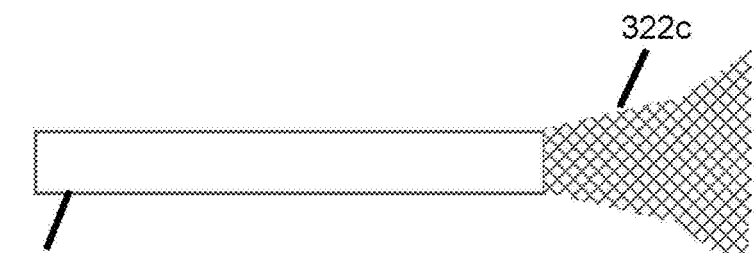
FIG. 27 illustrates a catheter with a trumpeted-shaped catch, according to one embodiment.

FIGS. 25-27 shows microcatheter 318 and catch/shield 322a-322c where the shield has a number of different shapes—the shield can take on a number of shapes including parabolic, linear, conical type profiles as shown in the figures. The shapes could take on the shape similar to that of a satellite dish (parabolic) or a noise-projecting megaphone (linear/conical type profile). Please note, the side profile of the shield is shown, and the shield sits around a distal portion of the microcatheter, so the shield sits radially around the microcatheter. FIG. 25 shows a truncated-conical type shield shape 322a where the distal portion of the shield expands radially out like the base of a cone, similar to a megaphone. In FIG. 26, shield 322b has a more elongated shape, where the proximal part of the shield tapers outward and the distal section of the shield has a relatively consistent shape and/or diameter. In FIG. 27, shield 322c adopts a more trumpeted shape. The shield could have one layer or multiple layers—for example a mesh could be folded back over onto itself, or folded under itself, to create a multiple layer mesh. Alternatively, multiple meshes could overlap and be attached together to create a multiple layer mesh. The shield could sit around the distal tip of the microcatheter, or sit around a point a bit proximal of the distal tip—but nonetheless should sit toward the distal region of the microcatheter. The distal end of the shield could sit flush with the distal tip of the microcatheter, sit past the distal tip of the microcatheter, or sit proximal of the microcatheter distal tip. Please note, the shield shapes are shown and described for illustrative ease, but in practice a number of different shapes could be used for shield 322.

Microcatheter 318 is delivered through a larger access or guide catheter, as described earlier. The larger access/guide catheter would provide the restraining force to collapse the shield during delivery. When microcatheter 318 is freed from the delivery catheter, the shield would adopt its natural unfurled shape. Preferably, the shield is comprised of material with good shape memory so this natural unfurled shape is set within the shield's shape memory. Nitinol, as discussed above, has good shape memory properties—in one example, the mesh shield 322 includes nitinol which is heat seat into its expanded shape. Once shield 322 is freed from the larger access/guide catheter, the shield will naturally adopt its expanded shape due to the imparted shape memory. In one embodiment, the shield configuration in the delivered and expanded state are similar—that is, in the delivered state when microcatheter 318 and shield 322 are housed within a larger guide catheter, the shield simply adopts a compressed position where it is pressed against microcatheter 318.

Shield 322 would then expand outward once said shield 322 is unconstrained by the guide/access catheter.

Figure 28:
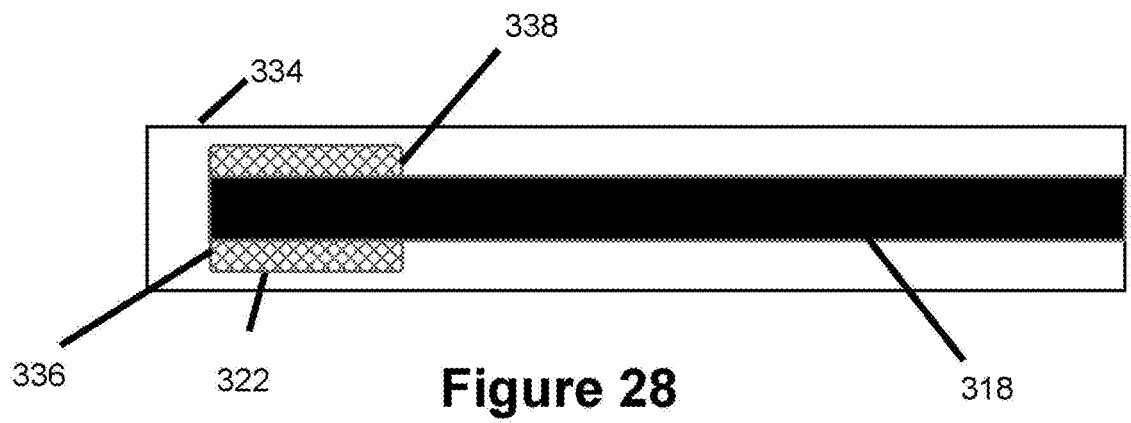
FIG. 28 illustrates a microcatheter with a catch structure being delivered through a larger guide or access catheter, according to one embodiment.
Figure 29:
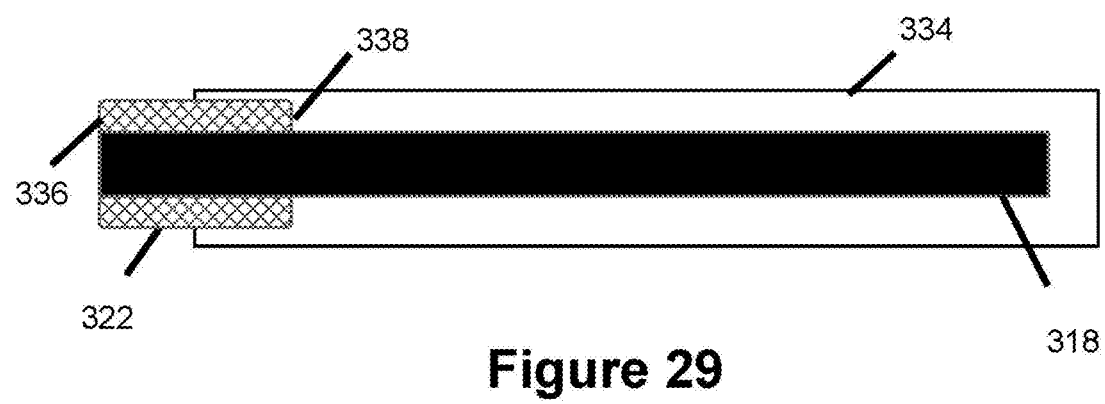
FIG. 29 illustrates a microcatheter with a catch in a partially delivered state through a larger guide or access catheter, according to one embodiment.
Figure 30:
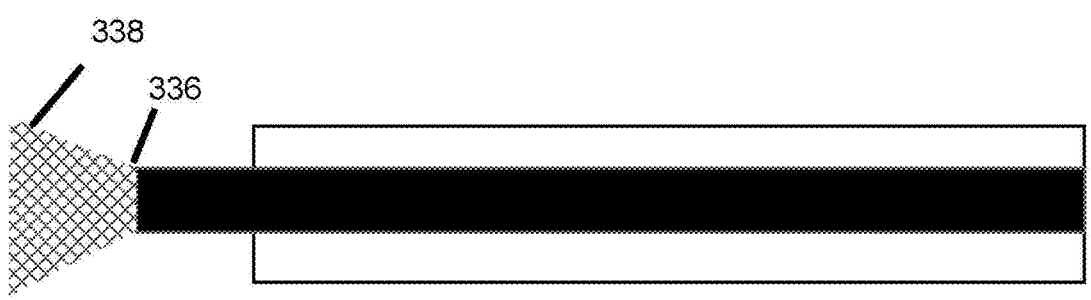
FIG. 30 illustrates a microcatheter with a catch in a delivered state where the embolic shield is free of the larger guide or access catheter, according to one embodiment.

In an alternate embodiment shown in FIGS. 28-30, shield 322 adopts a first inverted configuration while sheathed in the larger access/guide catheter 334, and a second unfurled position after being released from the said access/guide catheter 334. FIG. 28 shows microcatheter 318 with shield 322 attached to a distal portion of said microcatheter 318, within a larger access/guide catheter 334. Shield 322 is attached at location 336 to microcatheter 318. Section 338 of shield 322 represents what would be the distal part of shield 322 when said shield is fully expanded and free of the larger guide catheter 334—as shown in FIG. 30. When microcatheter 318 is housed within guide catheter 334, section 338 of shield 322 folds back and sits proximal relative to section 336, which is where the shield 322 is attached to microcatheter 318. FIG. 29 shows an in-between position where a portion of microcatheter 318 exits guide catheter 334, but the shield is still in an inverted position since the microcatheter 318 has not advanced to a point where the shield itself is free of larger guide catheter 334. Microcatheter 318 would be preloaded within guide catheter 334 so the shield adopts the inverted configuration, or the user could load microcatheter 318 through guide catheter 334, but the user would ensure this shield is inverted during placement.

In one embodiment, shield 322 is not detachable from microcatheter 318. With this embodiment, the liquid embolic would be delivered (as shown in FIG. 23). After the embolic is delivered through microcatheter 318 and solidifies, and any refluxed embolic is caught by shield 322, microcatheter 318 with integral shield 322 is withdrawn. However, generally it would be preferable to have a detachable shield so the user has the option of leaving the shield 322 in place to catch any embolic which might migrate in the future—or to address circumstances where the presence of the embolic in the shield may make retraction of shield 322 difficult.

In one embodiment shield 322 is detachable from microcatheter 318. The shield, if detached, would remain in the vasculature as an implant and the catheter would be withdrawn. However, the user could decide not to detach the shield—for instance, if confident that the embolic had solidified and would not migrate through the venous system, or if no embolic had refluxed and the shield was relatively free of embolic. Embolic would be delivered through microcatheter 318, and any migrating or refluxed embolic would be caught in shield 322. The user could detach shield 322 and retract microcatheter 318—leaving the shield in place in case any additional embolic migrates or refluxes. Shield 322 would therefore remain as a permanent implant. Alternatively, the user could decide not to detach shield 322 and instead retract microcatheter 318 along with connected shield 322. In one example, the user could retract microcatheter 318 and shield 322 through guide catheter 334; in another example, the user could retract a portion of microcatheter 318 through guide catheter 334 but leave shield 322 distal of the guide catheter and retract the system in this manner through the vasculature. Shield 322 is preferably made of biocompatible materials, such as the nitinol wires discussed earlier, since the shield would become an implant if detached. However, the shield could also be detached and subsequently retrieved.

Figure 31:
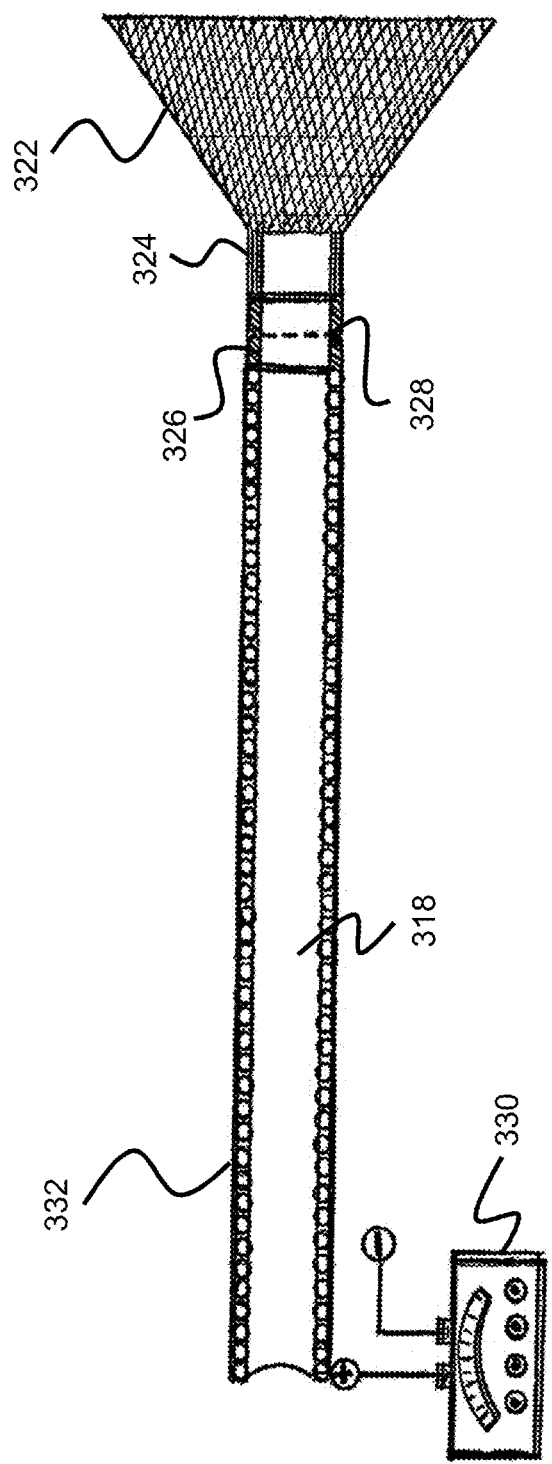
FIG. 31 illustrates a detachment system used to detach a catch from a catheter, according to one embodiment.

FIG. 31 shows a microcatheter 318, shield 322, and detachment system used to detach shield 322 from microcatheter 318. Shield 322 is preferably set near the distal tip of microcatheter 318. The distal part of shield 322, as discussed earlier, could sit flush with the distal tip of microcatheter 318, sit past the distal tip of microcatheter 318, or sit proximal of the microcatheter 318 distal tip. An electrolytic detachment system is shown in FIG. 31. Microcatheter 318 includes a metallic coil 332 which sits around the outer diameter of the microcatheter or is placed within the microcatheter 318 tube wall. The metallic coil can be made of a number of materials, such as stainless steel. The coil is used to provide structural strength to the catheter, and will also convey current through the coil. A voltage source 330 is placed at the proximal end of the system and provides a positive current source, in one example the voltage source is a DC power supply. An adhesive pad can be stuck to the patient, so the patient himself or herself (via the bloodstream) is the ground. The catheter metallic coil 332 culminates in a metallic (i.e. stainless steel) marker tube insert 326 which connects to coil 332. Shield 322 connects to a fused junction 324 which can be a polymeric or metallic element. The fused junction connects shield 322 to microcatheter 318 and can crimp over shield 322. The marker tube insert 326 contains a small laser-cut groove 328, this groove provides a thinned, weakened region in the insert which speeds up the electrolytic detachment of shield 322 from microcatheter 318. Anything distal of groove 328 should fall off and remain in the bloodstream along with shield 322 once the detachment sequence initiates. The electrolytic detachment occurs when the current from the power supply goes through coil 332, through the marker tube insert 326, through the patient bloodstream where the patient's blood provides the ionizing fluid media for the electrolytic detachment. When the detachment sequence initiates, microcatheter 318 and shield 322 are already in the blood vessel so they are already exposed to blood. The user would interact with the voltage source 330—in one example there can be a button or some user interface to detach shield 322 when desired.

Alternative embodiments could utilize other detachment systems—including mechanical, thermal, or other electrolytic concepts. For example, a mechanical system could be used where a screw can be rotated which would loosen a distal shield connection to effect shield detachment. Alternatively, a thermal detachment system could be used where the catheter structural coil 332 connects to a heater coil which sits over a tether, and the heater coil when heated severs the tether to detach the shield. Alternatively, a thermal detachment system could be used where an adhesive is heated and melts to effect detachment of the shield. Alternatively, the structural coil 332 could connect to a capsule element and the capsule element itself would contain either a severable tether or an electrolytically degradable linkage within said capsule to detach the shield. U.S. Pat. No. 8,182,506, US20060200192, US20100268204, US20110301686, US20150289879, US20151073772, US20150173773 all of which are hereby incorporated by reference in their entirety, disclose various detachment systems that could be used with the present concept. Different embodiments could also utilize a proximal battery with a positive and negative terminal, and catheter structural coils or wires running from the battery to shield 322 to the degradable linkage, where degradation of the degradable linkage detaches shield 322.

Figure 32:
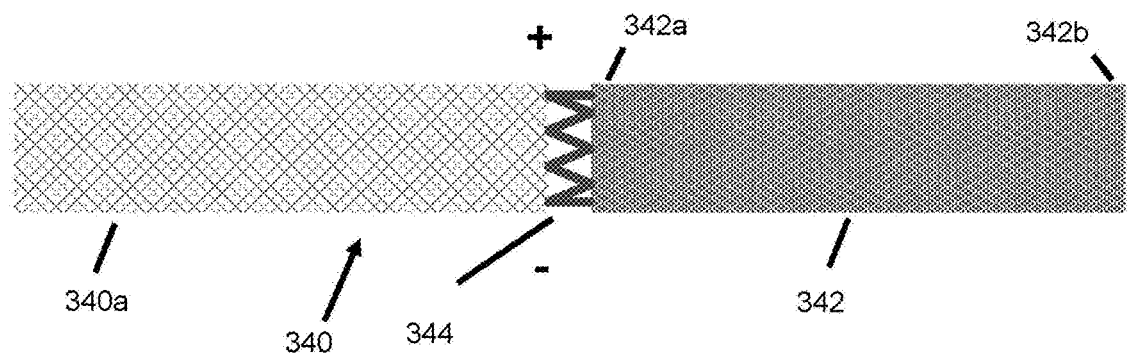
FIG. 32 illustrates a microcatheter with an attached collapsed catch, according to one embodiment.
Figure 33:
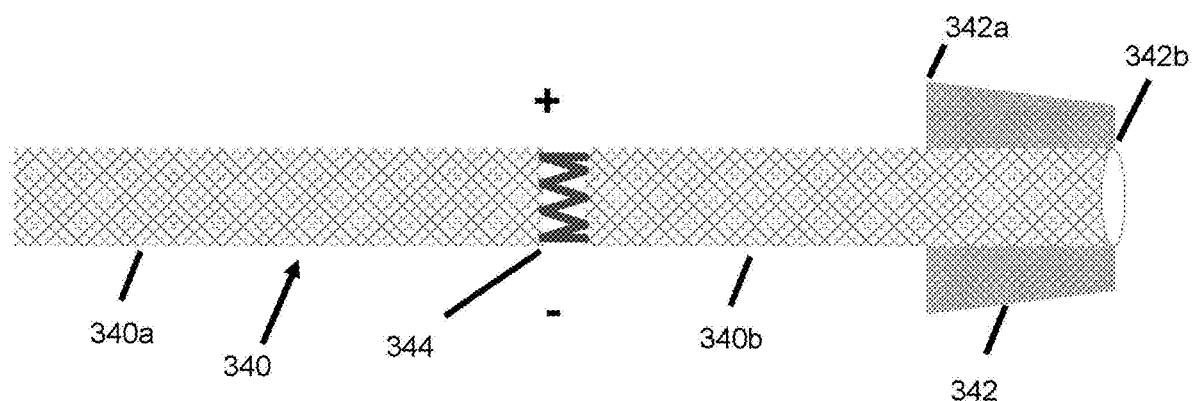
FIG. 33 illustrates the microcatheter and catch in FIG. 32 where part of the catch is no longer attached to the microcatheter, according to one embodiment.
Figure 34:
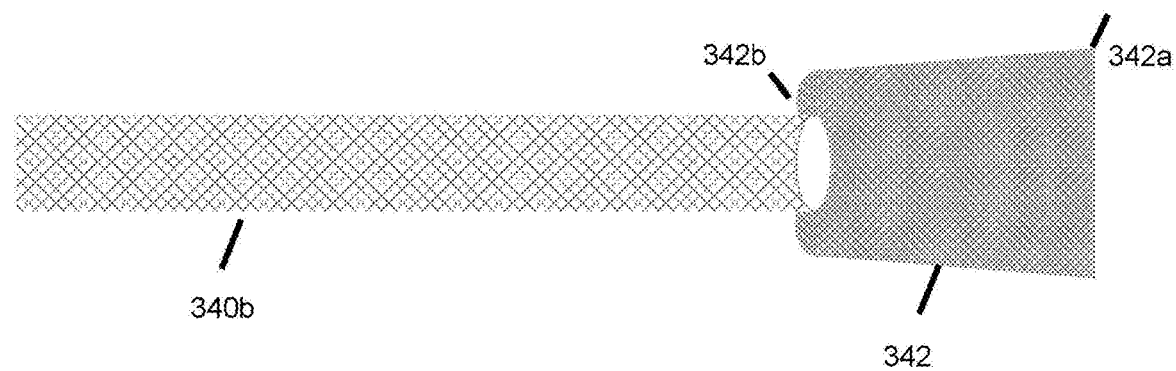
FIG. 34 illustrates the microcatheter and catch from FIG. 32 wherein the catch adopts an inverted configuration, according to one embodiment.

FIGS. 32-34 show an alternative embodiment involving a catch/shield structure which addresses potential friction issues that might otherwise arise when tracking a catch/shield structure through a larger access/guide catheter. This embodiment utilizes a mechanism to ensure a shield structure adopts a first elongated, collapsed state where it directly abuts the attached microcatheter during delivery, and then adopts an expanded shape later. In this embodiment, microcatheter 340 is structurally comprised of a braid of wires and part of the braid of wires ferries current from a proximal voltage source (e.g., a battery). One wire can supply positive current, while the other wire can supply negative current. In one example, a highly conductive material such as beryllium-copper can be used for the braid wires. Microcatheter 340 includes a proximal section 340a, a distal section 340b, and a heater element 344 in between. The heater 344 can be a laser-cut hypotube patterned in a circular shape with a serpentine pattern defining the circular shaped heater. The advantage of such a pattern is that the heat would be generated as the current travels through the serpentine shape around the circular pattern. Shield or catch structure 342 sits distal to this heater, where portion 342b is permanently attached to the distal tip of the microcatheter 340 and portion 342a is temporarily attached to a section of the microcatheter sitting near heater 344. Bonding polymeric material such as Engage, Pebax, or other low-melt temperature material can be used as the bonding material. When the heater 344 is heated, the bonding material near the heater melts and the shield adopts the shape shown in FIG. 33 as portion 342a of the shield is no longer bonded but portion 342b is still affixed to the distal tip of microcatheter 340. The physician can retract the microcatheter to cause the shield to invert and point distally as shown in FIG. 34—in this configuration portion 342b is still affixed to the distal tip of the microcatheter, however portion 342 now flips and sits distally past the microcatheter. The shield is preferably heat set into the shape shown in FIG. 34 to induce the shield to adopt this inverted shape once microcatheter 340 is retracted and after the portion of shield 342 is no longer affixed near heater 344. Shield 342 can be comprised of a nitinol braid and optionally coated with ePTFE, the inclusion of ePTFE on the shield—or the inclusion of ePTFE in shield section 342a—will help the bonding polymeric material hold the shield 342 in its collapsed state shown in FIG. 32.

Please note the various embodiments shown in FIGS. 1-34 and presented herein discussed various devices, systems, and methods used to prevent liquid embolic passage where liquid embolic is used for therapeutic effects in the vasculature—including for use in treating aneurysms and AVM's. All of the embodiments presented utilize a conduit to deliver liquid embolic, the conduit/conduits (e.g. microcatheter 130 of FIG. 1, pusher 230 of FIGS. 11-19, microcatheter 318 of FIG. 23) can be thought of as liquid embolic delivery conduit/conduits or liquid embolic delivery medium/media.

Please note any measurements, materials, drawings provided are meant to offer illustrative examples of the embodiments described herein and are not meant to expressly limit the embodiments to what is literally shown and/or recited. Though the embodiments were primarily presented for use with liquid embolic and offered particular advantages when used with liquid embolic in order to prevent liquid embolic migration, additional embolic agents such as embolic coils and embolic meshes could also be used where the devices would help prevent embolic agent migration.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of treating a neurovascular arteriovenous malformation comprising:
   providing a catheter with a mesh catch structure on the distal portion of the catheter, where the catheter is configured to deliver liquid embolic and dimethyl sulfoxide;
   configuring said catheter with said mesh catch structure to be tracked through the venous system and placed on the venous side of the arteriovenous malformation;
   delivering the liquid embolic and the dimethyl sulfoxide through the microcatheter and into the arteriovenous malformation;
   wherein said mesh catch structure has pores sized to allow the passage of the dimethyl sulfoxide but not allow the passage of the liquid embolic.

2. The method of claim 1 wherein said catheter includes a hub configured to attach to a syringe containing at least one of said liquid embolic and said dimethyl sulfoxide.

3. The method of claim 1 further comprising providing a syringe containing both liquid embolic and dimethyl sulfoxide in said syringe.

4. The method of claim 1 wherein said pores are sized from about 50 to about 250 microns.

5. The method of claim 1 wherein said pores are sized from about 100 to about 200 microns.

6. The method of claim 1 wherein said pores are sized from about 100 to about 150 microns.

7. A method of treating a neurovascular arteriovenous malformation comprising:
   tracking a guide catheter through the venous system of the vasculature;
   tracking a microcatheter with an attached distal mesh catch structure through the guide catheter and to the venous side of the arteriovenous malformation, where said distal mesh catch structure has pores sized to allow the passage of dimethyl sulfoxide but not allow the passage of liquid embolic;
   delivering liquid embolic and dimethyl sulfoxide through the microcatheter and into the arteriovenous malformation, where the microcatheter distal mesh catch structure catches any displaced liquid embolic while allowing passage of dimethyl sulfoxide.

8. The method of claim 7 wherein said liquid embolic and said dimethyl sulfoxide are contained in a common syringe configured to be mated to the microcatheter.

9. The method of claim 8 further comprising providing the common syringe containing said liquid embolic and said dimethyl sulfoxide.

10. The method of claim 7 wherein said pores are sized from about 50 to about 250 microns.

11. The method of claim 7 wherein said pores are sized from about 100 to about 200 microns.

12. The method of claim 7 wherein said pores are sized from about 100 to about 150 microns.

13. The method of claim 7 further comprising navigating said microcatheter through a draining vein of the neurovascular arteriovenous malformation.

14. A method of treating a neurovascular arteriovenous malformation comprising:
   tracking a first catheter to the arterial side of an arteriovenous malformation, said first catheter configured to deliver liquid embolic and dimethyl sulfoxide;
   tracking a second catheter to the venous side of an arteriovenous malformation, said second catheter having an attached distal mesh catch structure with pores sized to allow the passage of dimethyl sulfoxide but not allow the passage of liquid embolic;

delivering liquid embolic and dimethyl sulfoxide from the arterial side of the arteriovenous malformation through the first catheter.

15. The method of claim 14 further comprising tracking said first catheter through a feeder vessel of the neurovascular arteriovenous malformation.

16. The method of claim 14 wherein said liquid embolic and said dimethyl sulfoxide are contained in a common syringe configured to be mated to the first catheter.

17. The method of claim 16 further comprising providing the common syringe containing said liquid embolic and said dimethyl sulfoxide.

18. The method of claim 14 further comprising delivering liquid embolic and dimethyl sulfoxide from the venous side of the neurovascular arteriovenous malformation through the second catheter.

19. The method of claim 18 wherein said liquid embolic and said dimethyl sulfoxide are contained in a common syringe configured to be mated to the second catheter.

20. The method of claim 19 further comprising providing the common syringe containing said liquid embolic and said dimethyl sulfoxide.

* * * * *